(12) United States Patent
Kim et al.

(10) Patent No.: US 8,190,389 B2
(45) Date of Patent: May 29, 2012

(54) ADAPTER FOR ATTACHING ELECTROMAGNETIC IMAGE GUIDANCE COMPONENTS TO A MEDICAL DEVICE

(75) Inventors: Isaac J. Kim, San Jose, CA (US); Eric Goldfarb, San Francisco, CA (US); Ketan P. Muni, San Jose, CA (US); Joshua Makower, Los Altos, CA (US); Robert K. Deckman, San Bruno, CA (US)

(73) Assignee: Acclarent, Inc., Menlo Park, CA (US)

( * ) Notice: Subject to any disclaimer, the term of this patent is extended or adjusted under 35 U.S.C. 154(b) by 1388 days.

(21) Appl. No.: 11/436,897

(22) Filed: May 17, 2006

(65) Prior Publication Data

US 2008/0125720 A1 May 29, 2008

(51) Int. Cl.
*G01C 25/00* (2006.01)
*G06F 19/00* (2006.01)

(52) U.S. Cl. ............... 702/85; 33/501; 73/1.01; 73/1.79; 702/97

(58) Field of Classification Search ............ 33/501, 33/503, 504, 556, 559, 700, 701, 710; 73/1.01, 73/1.75, 1.76, 1.77, 1.79, 1.81, 865.8, 865.9, 73/866.5; 702/1, 85, 94, 95, 97, 127, 150, 702/152, 153, 154, 155, 158, 187, 189
See application file for complete search history.

(56) References Cited

U.S. PATENT DOCUMENTS

| | | | |
|---|---|---|---|
| 446,173 A | 2/1891 | Hancock | |
| 504,424 A | 9/1893 | De Pezzer | |
| 513,667 A | 1/1894 | Buckingham | |
| 705,346 A | 7/1902 | Hamilton | |
| 798,775 A | 9/1905 | Forsyth | |
| 816,792 A | 4/1906 | Green et al. | |
| 1,080,934 A | 12/1913 | Shackleford | |
| 1,200,267 A | 10/1916 | Sunnergren | |
| 1,650,959 A | 11/1927 | Pitman | |
| 1,735,519 A | 11/1929 | Vance | |
| 1,828,986 A | 10/1931 | Stevens | |
| 2,201,749 A | 5/1940 | Vandegrift | |
| 2,493,326 A | 1/1950 | Trinder | |
| 2,525,183 A | 10/1950 | Robison | |
| 2,847,997 A | 8/1958 | Tibone | |
| 2,899,227 A | 8/1959 | Gschwend | |
| 2,906,179 A * | 9/1959 | Bower | 409/80 |
| 2,995,832 A | 8/1961 | Alderson | |

(Continued)

FOREIGN PATENT DOCUMENTS

CH 668188 12/1988

(Continued)

OTHER PUBLICATIONS

Göttman, et al.; Balloon Dilation of Recurrent Ostial Occlusion of the frontal sinus; Abstract No. B-04353, European Congress of Radiology, Mar. 2001.

(Continued)

*Primary Examiner* — Edward Cosimano
(74) *Attorney, Agent, or Firm* — Steptoe & Johnson LLP

(57) ABSTRACT

Devices and methods wherein an adapter is used to attach an electromagnetic image guidance component to a medical device such that an electromagnetic image guidance system may be used to track the location of the medical device within the body of a human or animal subject.

7 Claims, 5 Drawing Sheets

U.S. PATENT DOCUMENTS

| | | | |
|---|---|---|---|
| 3,009,265 A | | 11/1961 | Bezark |
| 3,037,286 A | * | 6/1962 | Bower .................... 33/1 SB |
| 3,173,418 A | | 3/1965 | Baran |
| 3,347,061 A | | 10/1967 | Stuemky |
| 3,376,659 A | | 4/1968 | Asin et al. |
| 3,384,970 A | * | 5/1968 | Avalear .................... 33/503 |
| 3,435,826 A | | 4/1969 | Fogarty |
| 3,469,578 A | | 9/1969 | Bierman |
| 3,481,043 A | * | 12/1969 | Esch .......................... 33/505 |
| 3,486,539 A | | 12/1969 | Jacuzzi |
| 3,506,005 A | | 4/1970 | Gilio et al. |
| 3,509,635 A | * | 5/1970 | Meinke ...................... 33/561 |
| 3,515,888 A | * | 6/1970 | Lewis ................... 250/237 R |
| 3,527,220 A | | 9/1970 | Summers |
| 3,531,868 A | * | 10/1970 | Stevenson ................... 33/503 |
| 3,552,384 A | | 1/1971 | Pierie et al. |
| 3,624,661 A | | 11/1971 | Shebanow et al. |
| 3,731,963 A | | 5/1973 | Pond |
| 3,792,391 A | | 2/1974 | Ewing |
| 3,800,788 A | | 4/1974 | White |
| 3,802,096 A | | 4/1974 | Matern |
| 3,804,081 A | | 4/1974 | Kinoshita et al. |
| 3,834,394 A | | 9/1974 | Hunter et al. |
| 3,850,176 A | | 11/1974 | Gottschalk |
| 3,856,000 A | | 12/1974 | Chikama |
| 3,859,993 A | | 1/1975 | Bitner |
| 3,871,365 A | | 3/1975 | Chikama |
| 3,894,538 A | | 7/1975 | Richter |
| 3,903,893 A | | 9/1975 | Scheer |
| 3,910,617 A | | 10/1975 | Scalza et al. |
| 3,921,636 A | | 11/1975 | Zaffaroni |
| 3,948,254 A | | 4/1976 | Zaffaroni |
| 3,948,262 A | | 4/1976 | Zaffaroni |
| 3,967,618 A | | 7/1976 | Zaffaroni |
| 3,993,069 A | | 11/1976 | Buckles et al. |
| 3,993,072 A | | 11/1976 | Zaffaroni |
| 3,993,073 A | | 11/1976 | Zaffaroni |
| 4,016,251 A | | 4/1977 | Higuchi et al. |
| 4,052,505 A | | 10/1977 | Higuchi et al. |
| 4,053,975 A | | 10/1977 | Olbrich et al. |
| 4,069,307 A | | 1/1978 | Higuchi et al. |
| 4,102,342 A | | 7/1978 | Akiyama et al. |
| 4,138,151 A | | 2/1979 | Nakao |
| 4,184,497 A | | 1/1980 | Kolff et al. |
| 4,198,766 A | | 4/1980 | Camin et al. |
| 4,207,890 A | | 6/1980 | Mamajek et al. |
| 4,209,919 A | | 7/1980 | Kirikae et al. |
| 4,213,095 A | | 7/1980 | Falconer |
| 4,217,898 A | | 8/1980 | Theeuwes |
| 4,268,115 A | | 5/1981 | Slemon et al. |
| 4,299,226 A | | 11/1981 | Banka |
| 4,299,227 A | | 11/1981 | Lincoff |
| 4,338,941 A | | 7/1982 | Payton |
| D269,204 S | | 5/1983 | Trepp |
| 4,388,941 A | | 6/1983 | Riedhammer |
| RE31,351 E | | 8/1983 | Falconer |
| 4,435,716 A | | 3/1984 | Zandbergen |
| 4,437,856 A | | 3/1984 | Valli |
| 4,450,150 A | | 5/1984 | Sidman |
| 4,459,977 A | | 7/1984 | Pizon et al. |
| 4,464,175 A | | 8/1984 | Altman et al. |
| 4,471,779 A | | 9/1984 | Antoshkiw et al. |
| 4,499,899 A | | 2/1985 | Lyons, III |
| 4,554,929 A | | 11/1985 | Samson et al. |
| 4,564,364 A | | 1/1986 | Zaffaroni et al. |
| 4,571,239 A | | 2/1986 | Heyman |
| 4,571,240 A | | 2/1986 | Samson et al. |
| 4,581,017 A | | 4/1986 | Sahota |
| 4,585,000 A | | 4/1986 | Hershenson |
| D283,921 S | | 5/1986 | Dyak |
| 4,589,868 A | | 5/1986 | Dretler |
| 4,596,528 A | | 6/1986 | Lewis et al. |
| D284,892 S | | 7/1986 | Glassman |
| 3,393,073 A | | 7/1986 | Reutenauer et al. |
| 4,603,564 A | | 8/1986 | Kleinhany et al. |
| 4,606,346 A | | 8/1986 | Berg et al. |
| 4,607,622 A | | 8/1986 | Fritch et al. |
| 4,637,389 A | | 1/1987 | Heyden |
| 4,639,244 A | | 1/1987 | Rizk et al. |
| 4,645,495 A | | 2/1987 | Vaillancourt |
| 4,669,469 A | | 6/1987 | Gifford, III |
| 4,672,961 A | | 6/1987 | Davies |
| 4,675,613 A | | 6/1987 | Naegeli et al. |
| 4,691,948 A | | 9/1987 | Austin, Jr. et al. |
| 4,708,434 A | | 11/1987 | Tsuno |
| 4,708,834 A | | 11/1987 | Cohen et al. |
| 4,726,772 A | | 2/1988 | Amplatz |
| 4,736,970 A | | 4/1988 | McGourty et al. |
| 4,737,141 A | | 4/1988 | Spits |
| 4,748,869 A | | 6/1988 | Ohtsuka |
| 4,748,969 A | | 6/1988 | Wardle |
| 4,748,986 A | | 6/1988 | Morrison et al. |
| 4,755,171 A | | 7/1988 | Tennant |
| 4,771,776 A | | 9/1988 | Powell et al. |
| 4,795,439 A | | 1/1989 | Guest |
| 4,796,629 A | | 1/1989 | Grayzel |
| 4,803,076 A | | 2/1989 | Ranade |
| 4,811,743 A | | 3/1989 | Stevens |
| 4,815,478 A | | 3/1989 | Buchbinder et al. |
| 4,819,619 A | | 4/1989 | Augustine et al. |
| 4,846,186 A | | 7/1989 | Box et al. |
| 4,847,258 A | | 7/1989 | Sturm et al. |
| 4,851,228 A | | 7/1989 | Zentner et al. |
| 4,854,330 A | | 8/1989 | Evans, III et al. |
| 4,862,874 A | | 9/1989 | Kellner |
| 4,867,138 A | | 9/1989 | Kubota et al. |
| 4,883,465 A | | 11/1989 | Brennan |
| 4,897,651 A | | 1/1990 | DeMonte |
| 4,898,577 A | | 2/1990 | Badger et al. |
| 4,917,419 A | | 4/1990 | Mora, Jr. et al. |
| 4,917,667 A | | 4/1990 | Jackson |
| 4,919,112 A | | 4/1990 | Siegmund |
| 4,920,967 A | | 5/1990 | Cottonaro et al. |
| 4,925,445 A | | 5/1990 | Sakamoto et al. |
| 4,940,062 A | | 7/1990 | Hampton et al. |
| 4,943,275 A | | 7/1990 | Stricker |
| 4,946,466 A | | 8/1990 | Pinchuk et al. |
| 4,961,433 A | | 10/1990 | Christian |
| 4,966,163 A | | 10/1990 | Kraus et al. |
| 4,984,581 A | | 1/1991 | Stice |
| 4,994,033 A | | 2/1991 | Shockey et al. |
| 4,998,916 A | | 3/1991 | Hammerslag et al. |
| 4,998,917 A | | 3/1991 | Gaiser et al. |
| 5,001,825 A | | 3/1991 | Halpern |
| 5,002,322 A | | 3/1991 | Fukumoto |
| 5,019,075 A | | 5/1991 | Spears et al. |
| 5,019,372 A | | 5/1991 | Folkman et al. |
| 5,020,514 A | | 6/1991 | Heckele |
| 5,021,043 A | | 6/1991 | Becker et al. |
| 5,024,650 A | | 6/1991 | Hagiwara et al. |
| 5,024,658 A | | 6/1991 | Kozlov et al. |
| 5,026,384 A | | 6/1991 | Farr et al. |
| 5,030,227 A | | 7/1991 | Rosenbluth et al. |
| 5,041,089 A | | 8/1991 | Mueller et al. |
| 5,044,678 A | | 9/1991 | Detweiler |
| 5,053,007 A | | 10/1991 | Euteneuer |
| 5,055,051 A | | 10/1991 | Duncan |
| 5,060,660 A | | 10/1991 | Gambale et al. |
| 5,067,489 A | | 11/1991 | Lind |
| 5,069,226 A | | 12/1991 | Yamauchi et al. |
| 5,087,244 A | | 2/1992 | Wolinsky et al. |
| 5,087,246 A | | 2/1992 | Smith |
| 5,090,595 A | | 2/1992 | Vandoninck |
| 5,090,910 A | | 2/1992 | Narlo |
| 5,112,228 A | | 5/1992 | Zouras |
| 5,116,311 A | | 5/1992 | Lofstedt |
| 5,127,393 A | | 7/1992 | McFarlin et al. |
| 5,137,517 A | | 8/1992 | Loney et al. |
| 5,139,510 A | | 8/1992 | Goldsmith, III et al. |
| 5,139,832 A | | 8/1992 | Hayashi et al. |
| D329,496 S | | 9/1992 | Wotton |
| 5,152,747 A | | 10/1992 | Olivier |
| 5,163,989 A | | 11/1992 | Campbell et al. |
| 5,167,220 A | | 12/1992 | Brown |
| 5,168,864 A | | 12/1992 | Shockey |
| 5,169,043 A | | 12/1992 | Catania |
| 5,169,386 A | | 12/1992 | Becker et al. |

| | | | | | |
|---|---|---|---|---|---|
| 5,171,233 A | 12/1992 | Amplatz et al. | 5,533,985 A | 7/1996 | Wang |
| 5,180,368 A | 1/1993 | Garrison | 5,538,008 A | 7/1996 | Crowe |
| 5,183,470 A | 2/1993 | Wettermann | 5,546,964 A | 8/1996 | Stangerup |
| 5,189,110 A | 2/1993 | Ikematu et al. | 5,549,542 A | 8/1996 | Kovalcheck |
| 5,195,168 A | 3/1993 | Yong | 5,558,073 A | 9/1996 | Pomeranz et al. |
| 5,197,457 A | 3/1993 | Adair | 5,558,652 A | 9/1996 | Henke |
| 5,207,695 A | 5/1993 | Trout, III | 5,562,619 A | 10/1996 | Mirarchi et al. |
| 5,211,952 A | 5/1993 | Spicer et al. | 5,568,809 A | 10/1996 | Ben-haim |
| 5,215,105 A | 6/1993 | Kizelshteyn et al. | 5,578,007 A | 11/1996 | Imran |
| 5,221,260 A | 6/1993 | Burns et al. | 5,578,048 A | 11/1996 | Pasqualucci et al. |
| 5,226,302 A | 7/1993 | Anderson | 5,584,827 A | 12/1996 | Korteweg et al. |
| 5,230,348 A | 7/1993 | Ishibe et al. | 5,591,194 A | 1/1997 | Berthiaume |
| 5,236,422 A | 8/1993 | Eplett, Jr. | 5,599,284 A | 2/1997 | Shea |
| 5,243,996 A | 9/1993 | Hall | 5,599,304 A | 2/1997 | Shaari |
| D340,111 S | 10/1993 | Yoshikawa | 5,599,576 A | 2/1997 | Opolski |
| 5,250,059 A | 10/1993 | Andreas et al. | 5,601,087 A | 2/1997 | Gunderson et al. |
| 5,251,092 A | 10/1993 | Brady et al. | 5,601,594 A | 2/1997 | Best |
| 5,252,183 A | 10/1993 | Shaban et al. | 5,607,386 A | 3/1997 | Flam |
| 5,255,679 A | 10/1993 | Imran | 5,617,870 A | 4/1997 | Hastings et al. |
| 5,263,926 A | 11/1993 | Wilk | 5,626,374 A | 5/1997 | Kim |
| 5,264,260 A | 11/1993 | Saab | 5,633,000 A | 5/1997 | Grossman et al. |
| 5,267,965 A | 12/1993 | Deniega | 5,634,908 A | 6/1997 | Loomas |
| 5,270,086 A | 12/1993 | Hamlin | 5,638,819 A | 6/1997 | Manwaring et al. |
| 5,273,052 A | 12/1993 | Kraus et al. | 5,643,251 A | 7/1997 | Hillsman et al. |
| 5,275,593 A | 1/1994 | Easley et al. | 5,645,789 A | 7/1997 | Roucher, Jr. |
| 5,286,254 A | 2/1994 | Shapland et al. | 5,647,361 A | 7/1997 | Damadian |
| 5,295,694 A | 3/1994 | Levin | 5,656,030 A | 8/1997 | Hunjan et al. |
| 5,300,085 A | 4/1994 | Yock | 5,662,674 A | 9/1997 | Debbas |
| 5,304,123 A | 4/1994 | Atala et al. | 5,664,567 A | 9/1997 | Linder |
| 5,308,326 A | 5/1994 | Zimmon | 5,664,580 A | 9/1997 | Erickson et al. |
| 5,313,967 A | 5/1994 | Lieber et al. | 5,665,052 A | 9/1997 | Bullard |
| 5,314,417 A | 5/1994 | Stephens et al. | 5,669,388 A | 9/1997 | Vilkomerson |
| 5,315,618 A | 5/1994 | Yoshida | 5,673,707 A | 10/1997 | Chandrasekaran |
| 5,333,620 A | 8/1994 | Moutafis et al. | 5,676,673 A | 10/1997 | Ferre et al. |
| 5,334,167 A | 8/1994 | Cocanower | 5,679,400 A | 10/1997 | Tuch |
| 5,336,163 A | 8/1994 | DeMane et al. | 5,682,199 A | 10/1997 | Lankford |
| 5,341,818 A | 8/1994 | Abrams et al. | 5,685,838 A | 11/1997 | Peters et al. |
| 5,342,296 A | 8/1994 | Persson et al. | 5,685,847 A | 11/1997 | Barry |
| 5,343,865 A | 9/1994 | Gardineer et al. | 5,690,373 A | 11/1997 | Luker |
| 5,345,945 A | 9/1994 | Hodgson et al. | 5,693,065 A | 12/1997 | Rains, III |
| 5,346,075 A | 9/1994 | Nichols et al. | 5,694,945 A | 12/1997 | Ben-Haim |
| 5,346,508 A | 9/1994 | Hastings | 5,697,159 A | 12/1997 | Linden |
| 5,348,537 A | 9/1994 | Wiesner et al. | 5,700,286 A | 12/1997 | Tartaglia et al. |
| 5,350,396 A | 9/1994 | Eliachar | 5,707,389 A | 1/1998 | Louw et al. |
| 5,356,418 A | 10/1994 | Shturman | 5,708,175 A | 1/1998 | Koyanagi et al. |
| 5,368,049 A | 11/1994 | Raman et al. | 5,711,315 A | 1/1998 | Jerusalmy |
| 5,368,566 A | 11/1994 | Crocker | 5,713,839 A | 2/1998 | Shea |
| 5,372,138 A | 12/1994 | Crowley et al. | 5,713,946 A | 2/1998 | Ben-Haim |
| 5,372,584 A | 12/1994 | Zink et al. | 5,718,702 A | 2/1998 | Edwards |
| D355,031 S | 1/1995 | Yoshikawa | 5,720,300 A | 2/1998 | Fagan et al. |
| 5,386,817 A | 2/1995 | Jones | 5,722,401 A | 3/1998 | Pietroski et al. |
| 5,391,147 A | 2/1995 | Imran et al. | 5,722,984 A | 3/1998 | Fischell et al. |
| 5,391,179 A | 2/1995 | Mezzoli | 5,729,129 A | 3/1998 | Acker |
| 5,402,799 A | 4/1995 | Colon et al. | 5,730,128 A | 3/1998 | Pomeranz et al. |
| 5,409,444 A | 4/1995 | Kensey et al. | 5,733,248 A | 3/1998 | Adams et al. |
| 5,411,475 A | 5/1995 | Atala et al. | 5,752,513 A | 5/1998 | Acker et al. |
| 5,411,476 A | 5/1995 | Abrams et al. | 5,762,604 A | 6/1998 | Kieturakis |
| 5,411,477 A | 5/1995 | Saab | 5,766,158 A | 6/1998 | Opolski |
| 5,415,633 A | 5/1995 | Lazarus et al. | 5,775,327 A | 7/1998 | Randolph et al. |
| 5,425,370 A | 6/1995 | Vilkomerson | 5,776,158 A | 7/1998 | Chou |
| 5,439,446 A | 8/1995 | Barry | 5,779,699 A | 7/1998 | Lipson |
| 5,441,494 A | 8/1995 | Ortiz | 5,789,391 A | 8/1998 | Jacobus et al. |
| 5,441,497 A | 8/1995 | Narciso, Jr. | 5,792,100 A | 8/1998 | Shantha |
| 5,450,853 A | 9/1995 | Hastings et al. | 5,797,878 A | 8/1998 | Bleam |
| 5,451,221 A | 9/1995 | Cho et al. | 5,803,089 A | 9/1998 | Ferre et al. |
| 5,454,817 A | 10/1995 | Katz | 5,814,016 A | 9/1998 | Valley et al. |
| 5,458,572 A | 10/1995 | Campbell et al. | 5,819,723 A | 10/1998 | Joseph |
| 5,465,717 A | 11/1995 | Imran et al. | 5,820,568 A | 10/1998 | Willis |
| 5,465,733 A | 11/1995 | Hinohara et al. | 5,824,044 A | 10/1998 | Quiachon et al. |
| 5,486,181 A | 1/1996 | Cohen et al. | 5,824,048 A | 10/1998 | Tuch |
| 5,496,338 A | 3/1996 | Miyagi et al. | 5,824,173 A | 10/1998 | Fontirroche et al. |
| 5,497,783 A | 3/1996 | Urick et al. | 5,827,224 A | 10/1998 | Shippert |
| 5,507,301 A | 4/1996 | Wasicek et al. | 5,830,188 A | 11/1998 | Abouleish |
| 5,507,725 A | 4/1996 | Savage et al. | 5,833,608 A | 11/1998 | Acker |
| 5,507,766 A | 4/1996 | Kugo et al. | 5,833,645 A | 11/1998 | Lieber et al. |
| 5,512,055 A | 4/1996 | Domb et al. | 5,833,650 A | 11/1998 | Imran |
| 5,514,128 A | 5/1996 | Hillsman et al. | 5,833,682 A | 11/1998 | Amplatz et al. |
| 5,519,532 A | 5/1996 | Broome | 5,836,638 A | 11/1998 | Slocum |
| 5,531,676 A | 7/1996 | Edwards et al. | 5,836,935 A | 11/1998 | Ashton et al. |

| | | | |
|---|---|---|---|
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings et al. |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,195 A | 7/2000 | Ouchi |
| 6,109,268 A | 8/2000 | Thapliyal et al. |
| 6,113,567 A | 9/2000 | Becker |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedelmayer |
| 6,249,180 B1 | 6/2001 | Maalej et al. |
| 6,254,550 B1 | 7/2001 | McNamara et al. |
| 6,268,574 B1 | 7/2001 | Edens |
| 6,293,957 B1 | 9/2001 | Peters et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,348,041 B1 | 2/2002 | Klint |
| 6,352,503 B1 | 3/2002 | Matsui et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,511,418 B2 * | 1/2003 | Shahidi et al. ............ 600/117 |
| 6,514,249 B1 | 2/2003 | Maguire et al. |
| 6,517,478 B2 * | 2/2003 | Khadem ................ 600/117 |
| 6,524,299 B1 | 2/2003 | Tran et al. |
| 6,526,302 B2 | 2/2003 | Hassett |
| 6,527,753 B2 | 3/2003 | Sekine et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |

| | | |
|---|---|---|
| 6,596,009 B1 | 7/2003 | Jelic |
| 6,607,546 B1 | 8/2003 | Murken |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,652,472 B2 | 11/2003 | Jafari et al. |
| 6,652,480 B1 | 11/2003 | Imran et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,755,812 B2 | 6/2004 | Peterson et al. |
| 6,776,772 B1 | 8/2004 | Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,817,976 B2 | 11/2004 | Rovegno |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,927,478 B2 | 8/2005 | Paek |
| 6,939,361 B1 | 9/2005 | Kleshinski |
| 6,955,657 B1 | 10/2005 | Webler |
| 6,966,906 B2 | 11/2005 | Brown |
| 6,979,290 B2 | 12/2005 | Mourlas et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,011,654 B2 | 3/2006 | Dubrul et al. |
| 7,022,105 B1 | 4/2006 | Edwards |
| 7,043,961 B2 * | 5/2006 | Pandey et al. .................. 73/1.81 |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,316,168 B2 | 1/2008 | van der Knokke et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,361,168 B2 | 4/2008 | Makower et al. |
| 7,366,562 B2 | 4/2008 | Dukesherer et al. |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| D586,465 S | 2/2009 | Faulkner et al. |
| D586,916 S | 2/2009 | Faulkner et al. |
| 7,488,313 B2 | 2/2009 | Segal et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,559,925 B2 | 7/2009 | Goldfarb et al. |
| 7,625,335 B2 | 12/2009 | Deichmann et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,717,933 B2 | 5/2010 | Becker |
| 7,720,521 B2 * | 5/2010 | Chang et al. .................. 600/424 |
| 7,736,301 B1 | 6/2010 | Webler et al. |
| 7,740,642 B2 | 6/2010 | Becker |
| 7,753,929 B2 | 7/2010 | Becker |
| 7,799,048 B2 | 9/2010 | Hudson et al. |
| 7,837,672 B2 | 11/2010 | Intoccia |
| D630,321 S | 1/2011 | Hamilton, Jr. |
| D632,791 S | 2/2011 | Murner |
| 2001/0016684 A1 | 8/2001 | Shahidi |
| 2001/0023332 A1 | 9/2001 | Hahnen |
| 2001/0027307 A1 | 10/2001 | Dubrul et al. |
| 2001/0029317 A1 | 10/2001 | Hayakawa |
| 2001/0034530 A1 * | 10/2001 | Malackowski et al. ......... 606/130 |
| 2001/0051761 A1 * | 12/2001 | Khadem ....................... 600/117 |
| 2002/0002349 A1 | 1/2002 | Flaherty et al. |
| 2002/0006961 A1 | 1/2002 | Katz et al. |
| 2002/0010384 A1 * | 1/2002 | Shahidi et al. ................. 600/118 |
| 2002/0010426 A1 | 1/2002 | Clayman et al. |
| 2002/0016564 A1 | 2/2002 | Courtney et al. |
| 2002/0026155 A1 | 2/2002 | Mangosong |
| 2002/0029030 A1 | 3/2002 | Lurie et al. |
| 2002/0031941 A1 | 3/2002 | Cote et al. |
| 2002/0055746 A1 | 5/2002 | Burke et al. |
| 2002/0062133 A1 | 5/2002 | Gilson et al. |
| 2002/0077852 A1 | 6/2002 | Ford et al. |
| 2002/0082558 A1 | 6/2002 | Samson et al. |
| 2002/0082583 A1 | 6/2002 | Lerner |
| 2002/0090388 A1 | 7/2002 | Humes et al. |
| 2002/0107475 A1 | 8/2002 | Maginot |
| 2002/0116043 A1 | 8/2002 | Garibaldi et al. |
| 2002/0165521 A1 | 11/2002 | Cioanta et al. |
| 2003/0013985 A1 | 1/2003 | Saadat |
| 2003/0014036 A1 | 1/2003 | Varner et al. |
| 2003/0017111 A1 | 1/2003 | Rabito |
| 2003/0032942 A1 | 2/2003 | Theeuwes et al. |
| 2003/0040697 A1 | 2/2003 | Pass et al. |
| 2003/0069521 A1 | 4/2003 | Reynolds et al. |
| 2003/0069549 A1 | 4/2003 | MacMahon et al. |
| 2003/0073955 A1 | 4/2003 | Otawara |
| 2003/0073972 A1 | 4/2003 | Rosenman et al. |
| 2003/0083608 A1 | 5/2003 | Evans et al. |
| 2003/0083613 A1 | 5/2003 | Schaer |
| 2003/0100886 A1 | 5/2003 | Segal et al. |
| 2003/0109810 A1 | 6/2003 | Brennan et al. |
| 2003/0114732 A1 | 6/2003 | Webler et al. |
| 2003/0120339 A1 | 6/2003 | Banik et al. |
| 2003/0130598 A1 | 7/2003 | Manning et al. |
| 2003/0163154 A1 | 8/2003 | Miyata et al. |
| 2003/0164952 A1 | 9/2003 | Deichmann et al. |
| 2003/0171650 A1 | 9/2003 | Tartaglia et al. |

| | | |
|---|---|---|
| 2003/0181827 A1 | 9/2003 | Hojeibane et al. |
| 2003/0185872 A1 | 10/2003 | Kochinke |
| 2003/0208194 A1 | 11/2003 | Hovda et al. |
| 2003/0209096 A1* | 11/2003 | Pandey et al. .............. 73/865.9 |
| 2003/0225329 A1 | 12/2003 | Rossner et al. |
| 2004/0015150 A1 | 1/2004 | Zadno-Azizi |
| 2004/0018980 A1 | 1/2004 | Gurney et al. |
| 2004/0034311 A1 | 2/2004 | Mihalcik |
| 2004/0043052 A1 | 3/2004 | Hunter et al. |
| 2004/0058992 A1 | 3/2004 | Marinello et al. |
| 2004/0064083 A1 | 4/2004 | Becker |
| 2004/0064105 A1 | 4/2004 | Capes et al. |
| 2004/0064150 A1 | 4/2004 | Becker |
| 2004/0098017 A1 | 5/2004 | Saab et al. |
| 2004/0116958 A1 | 6/2004 | Gopferich et al. |
| 2004/0122471 A1 | 6/2004 | Toby et al. |
| 2004/0127820 A1 | 7/2004 | Clayman et al. |
| 2004/0158229 A1 | 8/2004 | Quinn |
| 2004/0167440 A1 | 8/2004 | Sharrow |
| 2004/0167442 A1 | 8/2004 | Shireman et al. |
| 2004/0167443 A1 | 8/2004 | Shireman et al. |
| 2004/0181175 A1 | 9/2004 | Clayman et al. |
| 2004/0193073 A1 | 9/2004 | DeMello et al. |
| 2004/0193139 A1 | 9/2004 | Armstrong et al. |
| 2004/0230095 A1 | 11/2004 | Stefanchik et al. |
| 2004/0230131 A1 | 11/2004 | Kassab et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0249267 A1 | 12/2004 | Gilboa |
| 2004/0254625 A1 | 12/2004 | Stephens et al. |
| 2004/0267347 A1 | 12/2004 | Cervantes |
| 2005/0027249 A1 | 2/2005 | Reifart et al. |
| 2005/0043706 A1 | 2/2005 | Eaton et al. |
| 2005/0049486 A1 | 3/2005 | Urquhart et al. |
| 2005/0055077 A1 | 3/2005 | Marco et al. |
| 2005/0059931 A1 | 3/2005 | Garrison et al. |
| 2005/0089670 A1 | 4/2005 | Large et al. |
| 2005/0107720 A1 | 5/2005 | Burmeister et al. |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0124856 A1 | 6/2005 | Fujikura et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228260 A1 | 10/2005 | Burwell et al. |
| 2005/0228412 A1 | 10/2005 | Surti |
| 2005/0234507 A1 | 10/2005 | Geske et al. |
| 2005/0240147 A1 | 10/2005 | Makower et al. |
| 2005/0244472 A1 | 11/2005 | Hughes et al. |
| 2005/0245906 A1 | 11/2005 | Makower et al. |
| 2005/0283221 A1 | 12/2005 | Mann et al. |
| 2005/0288549 A1 | 12/2005 | Mathis |
| 2005/0288759 A1 | 12/2005 | Jones et al. |
| 2006/0004286 A1* | 1/2006 | Chang et al. .............. 600/435 |
| 2006/0004323 A1 | 1/2006 | Chang et al. |
| 2006/0063973 A1 | 3/2006 | Makower et al. |
| 2006/0067982 A1 | 3/2006 | Haapakumpu et al. |
| 2006/0074318 A1 | 4/2006 | Ahmed et al. |
| 2006/0085027 A1 | 4/2006 | Santin et al. |
| 2006/0095066 A1 | 5/2006 | Chang et al. |
| 2006/0106361 A1 | 5/2006 | Muni et al. |
| 2006/0107957 A1 | 5/2006 | Djupesland |
| 2006/0116749 A1 | 6/2006 | Willink et al. |
| 2006/0149310 A1 | 7/2006 | Becker |
| 2006/0173382 A1 | 8/2006 | Schreiner |
| 2006/0190022 A1 | 8/2006 | Beyar et al. |
| 2006/0210605 A1 | 9/2006 | Chang et al. |
| 2006/0211752 A1 | 9/2006 | Kohn et al. |
| 2006/0271024 A1 | 11/2006 | Gertner et al. |
| 2007/0005094 A1 | 1/2007 | Eaton et al. |
| 2007/0020196 A1 | 1/2007 | Pipkin et al. |
| 2007/0049929 A1 | 3/2007 | Catanese, III et al. |
| 2007/0073269 A1 | 3/2007 | Becker |
| 2007/0112358 A1 | 5/2007 | Abbott et al. |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0208252 A1 | 9/2007 | Makower |
| 2007/0208301 A1 | 9/2007 | Evard et al. |
| 2007/0250105 A1 | 10/2007 | Ressemann et al. |
| 2007/0269385 A1 | 11/2007 | Yun et al. |
| 2007/0293727 A1 | 12/2007 | Goldfarb et al. |
| 2007/0293946 A1 | 12/2007 | Gonzales et al. |
| 2008/0015540 A1 | 1/2008 | Muni et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0082045 A1 | 4/2008 | Goldfarb et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125046 A1 | 5/2008 | Deng et al. |
| 2008/0125626 A1 | 5/2008 | Chang et al. |
| 2008/0154250 A1 | 6/2008 | Makower et al. |
| 2008/0154345 A1 | 6/2008 | Taylor |
| 2008/0187098 A1 | 8/2008 | Gertner et al. |
| 2008/0188870 A1 | 8/2008 | Andre et al. |
| 2008/0195041 A1 | 8/2008 | Goldfarb et al. |
| 2008/0208242 A1 | 8/2008 | Becker |
| 2008/0208243 A1 | 8/2008 | Becker |
| 2008/0215082 A1 | 9/2008 | Becker |
| 2008/0215083 A1 | 9/2008 | Becker |
| 2008/0228085 A1 | 9/2008 | Jenkins et al. |
| 2008/0234720 A1 | 9/2008 | Chang et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0047326 A1 | 2/2009 | Eaton et al. |
| 2009/0088728 A1 | 4/2009 | Dollar et al. |
| 2009/0093823 A1 | 4/2009 | Chang et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0192492 A1 | 7/2009 | Eaton et al. |
| 2009/0198216 A1 | 8/2009 | Muni et al. |
| 2009/0227945 A1 | 9/2009 | Eaton et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0087811 A1 | 4/2010 | Herrin et al. |
| 2010/0114066 A1 | 5/2010 | Makower et al. |
| 2010/0121308 A1 | 5/2010 | Muni et al. |
| 2010/0198191 A1 | 8/2010 | Clifford et al. |

FOREIGN PATENT DOCUMENTS

| | | |
|---|---|---|
| CN | 2151720 | 1/1994 |
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 0129634 | 1/1985 |
| EP | 0257605 | 3/1988 |
| EP | 0355996 | 2/1990 |
| EP | 0418391 | 3/1991 |
| EP | 0427852 | 5/1991 |
| EP | 0623582 | 11/1994 |
| EP | 0624349 | 11/1994 |
| EP | 0744400 | 11/1996 |
| EP | 0585757 | 6/1997 |

| | | |
|---|---|---|
| EP | 0893426 | 1/1999 |
| EP | 1042998 | 10/2000 |
| EP | 1166710 | 1/2002 |
| EP | 1413258 A1 | 4/2004 |
| FR | 2859377 A1 | 3/2005 |
| FR | 2916144 | 11/2008 |
| GB | 2125874 | 3/1984 |
| GB | 2305174 | 4/1997 |
| JP | 5367935 | 6/1978 |
| JP | 10-24098 | 1/1989 |
| JP | 3-504935 | 10/1991 |
| JP | 6-277296 | 10/1994 |
| JP | 07-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-526077 | 12/2001 |
| JP | 2002-028166 | 1/2002 |
| JP | 2002-508214 | 3/2002 |
| JP | 2002-538850 | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | 90/11053 | 10/1990 |
| WO | 90/14865 | 12/1990 |
| WO | 91/17787 | 11/1991 |
| WO | 92/15286 | 9/1992 |
| WO | 92/22350 | 12/1992 |
| WO | 94/12095 | 6/1994 |
| WO | 96/29071 | 9/1996 |
| WO | 97/24161 | 6/1997 |
| WO | 99/24106 | 5/1999 |
| WO | 99/30655 | 6/1999 |
| WO | 99/32041 | 7/1999 |
| WO | 00/09192 | 2/2000 |
| WO | 00/23009 | 4/2000 |
| WO | 00/53252 | 9/2000 |
| WO | 01/45572 | 6/2001 |
| WO | 01/56481 | 8/2001 |
| WO | W00154558 A2 | 8/2001 |
| WO | W00174266 A1 | 10/2001 |
| WO | 01/97895 | 12/2001 |
| WO | 02/062269 | 8/2002 |
| WO | 03/049603 | 6/2003 |
| WO | 03/105657 | 12/2003 |
| WO | 2004/006788 | 1/2004 |
| WO | 2004/018980 | 3/2004 |
| WO | 2004/026391 | 4/2004 |
| WO | 2004/082525 A2 | 9/2004 |
| WO | 2004/082525 A3 | 9/2004 |
| WO | 2005/018730 | 3/2005 |
| WO | 2005/077450 | 8/2005 |
| WO | 2005/089670 | 9/2005 |
| WO | 2006/034008 | 3/2006 |
| WO | 2006/078884 | 7/2006 |
| WO | 2006/107957 | 10/2006 |
| WO | 2006/116597 | 11/2006 |
| WO | 2006/118737 | 11/2006 |
| WO | 2006/135853 | 12/2006 |
| WO | 2007/111636 | 10/2007 |
| WO | 2007/124260 | 11/2007 |
| WO | 2008/036149 | 3/2008 |
| WO | 2008/045242 | 4/2008 |
| WO | 2008/051918 | 5/2008 |
| WO | 2008/134382 | 11/2008 |

OTHER PUBLICATIONS

Göttman, et al., Balloon dilatation of recurrent ostial occlusion of the front sinus; ECR, Mar. 2, 2001.
Göttman, et al., Successful Treatment of Recurrent Post-operative Frontal Sinus Stenoses by Balloon Dilatation; CIRSE, Oct. 5, 2002.
Göttman, et al., Balloon dilatation in the nasal cavity and paranasal sinuses; CIRSE, Sep. 25, 2004.
Robison, J. Mathews, M.D., Pressure Treatment of Purulent Maxillary Sinusitis, Texas State Journal of Medicine, May 1951, pp. 281-288.
Robison, J. Mathews, M.D., Pressure Treatment of Maxillary Sinusitis, J.A.M.A., May 31, 1952, pp. 436-440.
Strohm et al. Die Behandlung von Stenosen der oberen Luftwege mittels röntgenologisch gesteuerter Ballondilation Sep. 25, 1999.
Argon Medical. Maxxim Medical. Ad for Sniper EliteTM Hydrophilic Ni-Ti Alloy Guidewire (2001).
Aust, R., et al 'The Functional Size of the Human Maxillary Ostium in Vivo' Acta. Otolaryn. (1978) vol. 78 pp. 432-435.
Baim, D.S., MD *Grossman's Cardiac Catheterization, Angiography, and Intervention* (2000) Lippincott Williams & Wilkins pp. 76, 84 & 214.
Barrett, S. 'Be Wary of Neurocranial Restructuring (NCR)' Chirobase (available at: .chirobase.org/06DD/ncr.html) (Jul. 2003.).
Bartal, N. 'An Improved Stent for Use in the Surgical Management of Congenital Posterior Choanal Atresia' J. Laryngol. Otol. (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. inventors.about.com/library/inventors/blcatheter.htm?p=1.
Benninger et al. Adult Chronic Rhinosinusitis: Definitions, Diagnosis, Epidemiology, and Pathophysiology Arch Otolaryngol Head and Neck Surg. (Sep. 2003) vol. 129 pp. S1-S32.
Bent et al. 'The Frontal Cell as a Cause of Frontal Sinus Obstruction' American Journal of Rhinology. (1994) vol. 8, No. 4 pp. 185-191.
Binner et al. 'Fibre-Optic Transillumination of the Sinuses: A Comparison of the Value of Radiography and Transillumination in Antral Disease' Clinical Otolaryngology. (1978) vol. 3 pp. 1-11.
Brown, C.L. et al 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: The University of Miami Experience' American Journal of Rhinology (1998) vol. 12, No. 5 pp. 335-339.
Casserly, I.P. et al Chapter 7. 'Guides and Wires in Percutaneous Coronary Intervention' *Strategic Approaches in Coronary Intervention* (2006) Lippincott Williams & Wilkins pp. 91-99.
Chien, Y.W. et al. *Nasal Systemic Drug Delivery, Drugs and the Pharmaceutical Sciences* (1989) Marcel Dekker, Inc. Chapter 3, pp. 39-88.
Cohen et al 'Endoscopic Sinus Surgery: Where we are and where we're going' Current Opinion in Otolaryngology & Head and Neck Surgery (2005) vol. 13 pp. 32-38.
Colla, A. et al 'Trihaloacetylated Enol Ethers-General Synthetic Procedure and Heterocyclic Ring Closure Reactions with Hydroxylamine' Synthesis. (Jun. 1991) pp. 483-486.
Costa, M.N. et al 'Endoscopic Study of the Intranasal Ostium in External Dacryocystorhinostomy Postoperative. Influence of Saline Solution and 5Flurorouracil' Clinics. (2007) vol. 62, Issue 1 pp. 41-46. scielo.br/scielo.php?pid=S1807-59322007000100007&script=sci_arttext.
Davis, G.E. et al., 'A Complication From Neurocranial Restructuring' Arch Otolaryngology Head Neck Surg. (Apr. 2003) vol. 129 pp. 472-474.
Deutschmann, R. et al. 'A Contribution to the Topical Treatment of [Maxillary] Sinusitis Preliminary Communication' Stomat DDR 26, (1976) pp. 585-592.
Draf, W. 'Endonasal Micro-Endoscopic Frontal Sinus Surgery: the Fulda Concept' Op Tech Otolaryngol Head Neck Surg. (1991) vol. 2 pp. 234-240.
Edmond et al 'ENT Surgical Stimulator' Nov. 1998 Final Report Cooperative Agreement No. DAMD17-95-2-5023.
ENT Checklist; Physical Examination Performance Checklist.
Eremychev, V.A. 'Needles for Puncture and Drainage of the Maxillary Sinus' Meditsinskaya Tekhnika, No. 5 (1974) pp. 54-55.
Feldman, R.L. et al 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.

Ford, C.N. 'A Multipurpose Layngeal Injector Device' Otolaryngol. Head Neck Surg (1990) vol. 103, No. 1 pp. 135-137.

Friedman, M. M.D., et al 'Frontal Sinus Surgery: Endoscopic Technique' Operative Techniques in Otolarynology-Head and Neck Surgery. (Jun. 2001) vol. 12, No. 2 pp. 60-65.

Friedman, et al 'Intraoperative and Postoperative Assessment of Frontal Sinus Patency by Transillumination' Laryngoscope. (Apr. 2000) vol. 110 pp. 683-684.

Friedman et al 'Middle Turbinate Medialization and Preservation in Endoscopic Surgery' Otolaryngol. Head Neck Surg. (2000) vol. 123, No. 1, Part 1. pp. 76-80.

Fung, M.K.T. 'How I Do It—Head and Neck and Plasic Surgery. A Targeted Problem and its Solution. Template for Frontal Osteoplastic Flap' Laryngoscope. (1986) vol. 96 pp. 578-579.

Gatot, A. et al., 'Early Treatment of Orbital Floor Fractures with Catheter Balloon in Children' Int. J. Pediatric Otorhinolaryngol (1991) vol. 21 pp. 97-101.

Gerus, I.I. et al 'β-Ethoxyvinyl Polyfluroroalkyl Ketones-Versatile Synthones in Fluoroorganic Chemistry' Journal of Fluorine Chemistry. (1994) vol. 69 pp. 195-198. Elsevier Science S.A.

Good, R.H. 'An Intranasal Method for Opening the Frontal Sinus Establishing the Largest Possible Drainage' Laryngoscope. (1908) vol. 18 pp. 266-274.

Gopferich 'Polymer Degradation and Erosion: Mechanisms and Applications' Eur. J. Pharm. Biophar. (1996) vol. 42 pp. 1-11.

Gorlov, D.V. et al 'Acylation of 2-Methoxypropene with Anhydrides and Halides of Perflurocarboxylic Acids in the Presence of Tertiary Amines' Russian Chemical Bulletin. (Sep. 1999) vol. 48 No. 9 pp. 1791-1792. Kluwer Academic/Plenum Publishers.

Gottman, et al. 'Balloon Dilatation of Recurrent Ostial Occlusion of the Front Sinus' Abstract No. B-04353. European Congress of Radiology. (Mar. 2, 2001).

Gupta, D. et al 'Dacryocystitis Secondary to an Iatrogenic Foreign Body in the Lacrimal Apparatus' Ear, Nose & Throat Journal (2009) findarticles.com/p/articles/mi_m0BUM/is_7_88/ai_n32428620/.

Hashim, et al 'Balloon Compression of the Intermaxillary Sinus for Intractable Post Traumatic Bleeding from the Maxillary Artery' Scandinavian Journal of Plastic and Reconstructive Surgery and Hand Surgery (1999) vol. 33 pp. 321-324.

Hojo, M. et al 'Electrophilic Substitutions of Olefinic Hydrogens II. Acylation of Vinyl Ethers and N Vinyl Amides' Chemistry Letters (1976) pp. 499-502.

Hopf, J.U.G. et al 'Miniature Endoscopes in Otorhinolaryngologic Applications' Min Invas Ther & Allied Technol (1998) vol. 7, No. 3 pp. 209-218.

Hosemann, W. et al *A Dissection Course on Endoscopic Endonasal Sinus Surgery* (2005) Endo-Press, Tuttlingen pp. 4-37.

Hosemann, W. et al 'Endonasal Frontal Sinusotomy in Surgical Management of Chronic Sinusitis: A Critical Evaluation' American Journal of Rhinology (1997) vol. 11, No. 1 pp. 1-9.

Hosemann, M.E. et al 'Experimentelle Untersuchungen zur Wundheilung in den Nasennebenholhlen. II. Spontaner Wundschluss and medikamentose Effekte im standardisierten Wundmodell.' HNO 39 (1991) pp. 48-54.

Hosemann, M.E. et al 'Normal Wound Healing of the Paranasal Sinuses—Clinical and Experimental Investigations' Eur Arch Otorhinolaryngol. (1991) vol. 248 pp. 390-394.

Hospital Corpsman Sickcall Screener's Handbook. Naval Hospital Great Lakes (Apr. 1999) brooksidepress.org/Products/Operationa. Medicine/DATA. 2001 pp. 1-6.

Hybels, R.L. 'Transillumination During Osteoplastic Frontal Sinusotomy' The Laryngoscope (Sep. 1981) vol. 91 pp. 1560.

Ijaduola, T.G.A. 'Use of a Foley Catheter for Short-Term Drainage in Frontal Sinus Surgery' The Journal of Laryngology and Otology. (1989) vol. 103 pp. 375-378.

Iro, H. et al 'A New Device for Frontal Sinus Endoscopy: First Clinical Report' Otolaryngol. Head Neck Surg (2001) vol. 125 No. 6 pp. 613-616.

Jacobs, J.B. '100 Years of Frontal Sinus Surgery' Laryngoscope. (1997) vol. 107 pp. 1-36.

Kennedy, D.W., M.D. et al *Diseases of the Sinuses Diagnosis and Management* (Copyright 2001) by B.C. Decker Inc.

Khomutov, S.M. et al 'Dissolution of a Mixture of Steroids in Cyclodextrin Solutions: a Model Description' Pharmaceutical Chemistry Journal. (Nov. 2001) vol. 35, No. 11 pp. 627-629.

Kingdom, T.T. et al 'Image-Guided Surgery of the Sinuses: Current Technology and Applications' Otolaryngol. Clin. North Am. (Apr. 2004) vol. 37, No. 2 pp. 381-400.

Klossek, J.M. et al 'Local Safety of Intranasal Triamcinolone Acetonide: Clinical and Histological Aspects of Nasal Mucosa in the Long-Term Treatment of Perennial Allergic Rhinitis' Rhinology (2001) vol. 39, No. 1 pp. 17-22.

Kozlov et al 'Diagnosis and Treatment of Sinusitis by Yamik Sinus Catheters' Rhinology (1996) vol. 34. pp. 123-124.

Kuhn, et al. 'The Agger Nasi Cell in Frontal Recess Obstruction: An Anatomic, Radiology and Clinical Correlation' Operative Techniques in Otolaryngology—Head and Neck Surgery (1991) vol. 2, No. 4 pp. 226-231.

Laliberte F. et al 'Clinical and Pathologic Methods to Assess the Long-Term Safety or Nasal Corticosteroids' Allergy (2000) vol. 55, No. 8 pp. 718-722.

Lang, E.V. et al 'Access Systems for Puncture at an Acute Angle' J. Vasc. Interv. Radiol. (1995) vol. 6, No. 5 pp. 711-713.

Lanza, D.C. 'Postoperative Care and Avoiding Frontal Recess Stenosis' International Advanced Sinus Symposium. General Session Abstracts. Jul. 21-24, 1993.

Large, G.C. 'Crystalline Tetracycline Hydrochloride in the Treatment of Acute and Chronic Maxillary Sinusitis' Canad. M. A. J. (1958) vol. 79 pp. 15-16.

Lund, V.J. 'Maximal Medical Therapy for Chronic Rhinosinusitis' Otolaryngol Clin N Am. (2005) vol. 38 pp. 1301-1310.

Maran, A.G.D. et al 'The Use of the Foley Catheter in the Tripod Fracture' J. Laryngol. Otol (1971) vol. 85, Issue 9 pp. 897-902.

May, M. et al 'Frontal Sinus Surgery: Endonasal Drainage Instead of an External Osteopolstic Approach' Op Tech Otolaryngo Head Neck Surgery (1995) vol. 6, No. 3 pp. 184-192.

Medtronic, xomed.com-MicroFrance Catalog Browser. xomcat.com/xomfrance/index.php?zone=both&cat=18&sub=58&prodline=1272 (Dec. 31, 2003) pp. 1-2.

Mehan, V.K. et al 'Coronary Angioplasty through 4 French Diagnostic Catheters' Cathet. Cardiovasc. Diagn. (1993) vol. 30, No. 1 pp. 22-26.

Mellor, J.M. et al 'Synthesis of Trifluromethylnaphthalenes' Tetrahedron (2000) vol. 56 pp. 10067-10074. Elseview Science Ltd.

Metson, R. et al 'Endoscopic Treatment of Sphenoid Sinusitis' Otolaryngol. Head Neck Surg (1996) vol. 114, No. 6 pp. 736-744.

Metson, R. 'Holmium: Yag Laser Endoscopic Sinus Surgery: A Randomized Controlled Study' Laryngoscope (Jan. 1996) vol. 106, Issue 1, Supplement 77 pp. 1-18.

Miller et al. 'Management of Fractures of the Supraorbital Rim' Journal of Trauma (Jul. 1978) vol. 18, No. 7 pp. 507-512.

Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope (Aug. 1995) vol. 105 pp. 835-842.

Mols, B. 'Moveable Tool Tip for Keyhole Surgery' Delft Outlook (2005) vol. 3 pp. 13-17.

Mooney, M.R. et al 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.

Moriguchi, T. et al 'Addition-Elimination Reaction in the Trifluoroacetylation of Electron-Rich Olefins' J. Org. Chem. (1995) vol. 60, No. 11 pp. 3523-3528. American Chemical Society.

Piccirillo, J.F. et al 'Psychometric and Clinimetric Validity of the 20-Item Sino-Nasal Outcome Test (SNOT-20)' Otolaryngol. Head Neck Surg (2002) vol. 126, No. 1 pp. 41-47.

Piers, et al 'A Flexible Distal Tip with Two Degrees of Freedom for Enhanced Dexterity in Endoscopic Robot Surgery' Proceedings 13th Micromechanics Europe Workshop (2002) pp. 271-274.

Podoshin, L. et al 'Balloon Technique for Treatment of Frontal Sinus Fractures' The Journal of Laryngology & Otology (1967), vol. 81. pp. 1157-1161.

Pownell, P.H. et al 'Diagnostic Nasal Endoscopy' Plastic & Reconstructive Surgery (1997) vol. 99, Iss. 5 pp. 1451-1458.

Prince et al 'Analysis of the Intranasal Distribution of Ointment' J Otolaryngol. (1997) vol. 26 pp. 357-360.
Ramsdale, D.R. *Illustrated Coronary Intervention A case-oriented approach* (2001) Martin Dunitz Ltd. pp. 1-5.
Ritter, F.N. et al *Atlas of Paranasal Sinus Surgery* (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine. (May 1951) pp. 281-288.
Sama, A. et al 'Current Opinions on the Surgical Management of Frontal Sinus Disease' Ent News. pinpointmendical.com/ent-news (2009) vol. 17 No. 6 pp. 60-63.
Sanborn, T.A., et al 'Percutaneous Endocardial Transfer and Expression of Genes to the Myocardium Utilizing Fluropscopic Guidance' Catheter Cardiovasc. Interv. (2001) vol. 52, No. 2 pp. 260-266.
*Sawbones Catalog* 2001, Pacific Research Laboratories, Inc., Vashon, Washington 98070 USA.
Saxon, R.R., et al 'Technical Aspects of Accessing the Portal Vein During the Tips Procedure' J. Vasc. Interv. Radiol. (1997) vol. 8, No. 5 pp. 733-744.
Schaefer, S.D., M.D. *Rhinology and Sinus Disease A Problem-Oriented Approach* (Copyright 1988) by Mosby, Inc.
Schneider. Pfizer Ad for Softip.
Shah, N. J. et al 'Endoscopic Pituitary Surgery—A Beginner's Guide' Indian Journal of Otolaryngology and Head and Neck Surgery (2004) vol. 56, No. 1 pp. 71-78.
Shah, N. J. 'Functional Endoscopic Sinus Surgery' (1999); found at bhj.org/journal/1999_4104_oct99/sp—659.htm.
Single-Pole and Multi-Pole Lightguides for UV Spot Light Curing Systems. dymax.com/products/curing_equipment/lightguids/light. (2004) pp. 1-2.
Sobol, et al 'Sinusitis, Maxillary, Acute Surgical Treatment.' eMedicine. Retrieved from the Internet: <<emedicine.medscape.com/article/862030-print>> (Nov. 16, 2010) pp. 1-11.
St. Croix, et al 'Genes Expressed in Human Tumor Endothelium' Science (May 15, 2000) vol. 289 pp. 1197-1202.
Stammberger H. 'Komplikationen entzundlicher Nasennebenhohlenerkrankungen eischließlich iatrogen bedingter Komplikationen.' Eur Arch Oti-Rhino-Laryngol Suppl. (Jan. 1993) pp. 61-102.
Stammberger, et al 'Special Endoscopic Anatomy of the Lateral Nasal Wall and Ethmoidal Sinuses ' Functional Endoscopic Sinus Surgery. (1991) Ch. 3, pp. 49-87.
Strohm et al Die Behandlung von Stenosen der oberen Luftwege mittels rontgenologisch gesteuerter Ballondilation (Sep. 25, 1999) pp. 1-4.
Strohm, et al 'Le Traitenment Des Stenoses Voies Aeriennes Superieures Par Dilation Au Balloon' Sep. 25, 1999.
SurgTrainer Product Information 'Incisive Human Nasal Model for ESS Training' Surg Trainer, Ltd. Ibaraki, Japan (2004) 1.accsnet.ne.jp/~juliy/st/en/partslist.html.
Tabor, M.H. et al 'Symptomatic Bilateral Nasolacrimal Duct Cysts in a Newborn-Rhinoscopic Clinic' Ear, Nose & Throat Journal (2003) findarticles.com/p/articles/mi_m0BUM/is_2_82/ai_98248244 pp. 1-3.
Terumo. Medi-Tech. Boston Scientific. (1993) Ad for Glidewire.
The Operating Theatre Journal (otjonline.com) 'Disposable Medical Device for Wound Disclosure/The Tristel Purple Promotion—A Collaboration between Tristel plc and Karl Storz Endoscopy (UK) Ltd.' pp. 4.
Weber, R. et al 'Endonasale Stirnhohlenchirugie mit Langzeiteinlage eines Platzhalters' Laryngol. Rhinol. Otol. (1997) vol. 76 pp. 728-734. (English Abstract).
Weber, R. et al 'Videoendoscopic Analysis of Nasal Steroid Distribution' Rhinology (1999) vol. 37 pp. 69-73.
Weiner, R.I., D.O. et al 'Development and Application of Transseptal Left Heart Catheterization' Cathet. Cardiovasc. Diagn. (1988) vol. 15, No. 2 pp. 112-120.
Wiatrak, B.J. et al 'Unilateral Choanal Atresia: Initial Presentation and Endoscopic Repair' International Journal of Pediatric Otorhinolaryngology (1998) vol. 46 pp. 27-35.
Woog, et al. 'Paranasal Sinus Endoscopy and Orbital Fracture Repair' Arch Ophthalmol. (May 1998) vol. 116 pp. 688-691.
Wormald, P.J. et al 'The 'Swing-Door' Technique for Uncinectomy in Endoscopic Sinus Surgery' The Journal of Laryngology and Otology (1998) vol. 112 pp. 547-551.
Xomed-Treace. Bristol-Myers Squibb. Ad for Laser Shield II. Setting the Standards for Tomorrow.
Yamauchi, Y. et al 'Development of a Silicone Model for Endoscopic Sinus Surgery' proc International Journal of Computer Assisted Radiology and Surgery (1999) vol. 99 pp. 1039.
Yamauchi, Y. et al 'A Training System for Endoscopic Sinus Surgery with Skill Evaluation' Computer Assisted Radiology and Surgery (2001) with accompanying copy of poster presentation.
Yanagisawa et al 'Anterior and Posterior Fontanelles.' Ear, Nose & Throat Journal (2001) vol. 80. p. 10-12.
Zimarino, M., MD et al 'Initial Experience with the EuropassTM: A New Ultra-Low Profile Monorail Balloon Catheter' Cathet. Cardiovasc. Diagn. (1994) vol. 33, No. 1 pp. 76-79.
invotec.net/rhinology/ksplint.html. K-Splint Internal Nasal Splints; Jan. 25, 2007.
doylemedical.com/nasalsplints.htm; Doyle Nasal Splints; Jan. 25, 2007.
w.technologyforlife.com.au/ent/nasal.html; Nasal Surgery and Accessories; Jan. 25, 2007.
EP Communication dated Sep. 4, 2008 re: EP 05773189.
EP Communication dated Jun. 19, 2009 re: EP 05773189.
Examination Report dated Feb. 22, 2006 re: 02716734.5.
Examination Report dated Feb. 8, 2007 re: 02716734.5.
Examiners First Report dated Apr. 8, 2010 re: AU2005274794.
European Search Report and Search Opinion dated Sep. 11, 2009 from EP06815174.
International Preliminary Report on Patentability dated Aug. 25, 2006 from PCT/US05/25371.
International Preliminary Report on Patentability dated Nov. 27, 2008 from PCT/US07/11449.
International Preliminary Report on Patentability dated Apr. 16, 2009 from PCT/US07/021170.
International Preliminary Report on Patentability dated May 14, 2009 from PCT/US06/36960.
International Preliminary Report on Patentability dated Oct. 22, 2009 from PCT/US08/059786.
International Preliminary Report on Patentability dated Nov. 5, 2009 from PCT/US08/061343.
International Search Report dated May 23, 2002 from PCT/EP02/01228.
International Search Report and Written Opinion dated Apr. 10, 2006 from PCT/US05/25371.
International Search Report dated May 8, 2007 from PCT/US2006/16026.
International Search Report and Written Opinion dated Aug. 17, 2007 from PCT/US05/13617.
International Search Report and Written Opinion dated Aug. 29, 2007 from PCT/US06/002004.
International Search Report dated Sep. 25, 2007 from PCT/US06/37167.
International Search Report dated Oct. 19, 2007 from PCT/US07/03394.
International Search Report and Written Opinion dated May 29, 2008 from PCT/US07/021170.
International Search Report dated May 29, 2008 from PCT/US07/21922.
International Search Report and Written Opinion dated Jul. 1, 2008 from PCT/US06/22745.
International Search Report dated Jul. 3, 2008 from PCT/US2006/029695.
International Search Report dated Jul. 7, 2008 from PCT/US07/16213.
International Search Report dated Jul. 8, 2008 from PCT/US07/11474.
International Search Report and Written Opinion dated Jul. 17, 2008 from PCT/US06/36960.
International Search Report and Written Opinion dated Jul. 21, 2008 from PCT/US05/33090.

International Search Report dated Aug. 25, 2008 from PCT/US2008/0009111.
International Search Report dated Sep. 10, 2008 dated PCT/US07/16212.
International Search Report and Written Opinion dated Sep. 12, 2008 from PCT/US07/16214.
International Search Report and Written Opinion dated Sep. 17, 2008 from PCT/US08/059786.
International Search Report and Written Opinion dated Sep. 17, 2008 from PCT/US08/061343.
International Search Report and Written Opinion dated Oct. 1, 2008 from PCT/US07/11449.
International Search Report dated Oct. 15, 2008 from PCT/US2008/061048.
International Search Report from PCT Application No. PCT/US2009/057203 dated Nov. 30, 2009 as issued by the European Patent Office as searching authority.
International Search Report dated Dec. 10, 2009 re: PCT/US2009/052236.
International Search Report dated Dec. 16, 2009 re: PCT/US2009/050800.
International Search Report dated Jul. 8, 2010 re: PCT/US2010/027837.
International Search Report dated Oct. 6, 2010 re: PCT/US2010/040548.
International Search Report dated Mar. 25, 2011 re: PCT/US2010/062161.
International Search Report dated Mar. 28, 2011 re: PCT/US2010/061850.
Partial European Search Report dated Sep. 20, 2007 re: 07252018.
Partial European Search Report dated Mar. 25, 2008 re: 07252018.
Supplemental European Search Report dated Jun. 2, 2008 re: EP05773189.
Supplemental European Search Report dated Jan. 29, 2010 from EP07836108.
Supplemental European Search Report dated Feb. 2, 2010 re: EP07836109.
Supplemental European Search Report dated Feb. 17, 2010 re: EP07836110.
Supplemental European Search Report dated Mar. 1, 2010 re: EP05778834.
Supplemental European Search Report dated Mar. 16, 2010 from EP06718986.
Supplemental European Search Report dated Jun. 22, 2010 re: EP06784759.
Supplemental European Search Report dated Sep. 23, 2010 re: EP08746715.
Supplemental Partial European Search Report dated Nov. 19, 2010 re: EP06751637.
Supplemental European Search Report dated Jan. 28, 2011 from 07777004.
U.S. Appl. No. 10/259,300, filed Sep. 30, 2002.
U.S. Appl. No. 10/259,630, filed Sep. 30, 2002.
U.S. Appl. No. 10/470,881, filed Feb. 4, 2004.
U.S. Appl. No. 10/829,917, filed Apr. 21, 2004.
U.S. Appl. No. 10/912,578, filed Aug. 4, 2004.
U.S. Appl. No. 10/944,270, filed Sep. 17, 2004.
U.S. Appl. No. 11/037,548, filed Jan. 18, 2005.
U.S. Appl. No. 11/116,118 filed, Apr. 26, 2005.
U.S. Appl. No. 11/150,847, filed Jun. 10, 2005.
U.S. Appl. No. 11/193,020, filed Jul. 29, 2005.
U.S. Appl. No. 11/234,395, filed Sep. 23, 2005.
U.S. Appl. No. 11/347,147, filed Feb. 2, 2006.
U.S. Appl. No. 11/355,512, filed Feb. 16, 2006.
U.S. Appl. No. 11/436,892, filed May 17, 2006.
U.S. Appl. No. 11/438,090, filed May 18, 2006.
U.S. Appl. No. 11/522,497, filed Sep. 15, 2006.
U.S. Appl. No. 11/527,773, filed Sep. 25, 2006.
U.S. Appl. No. 11/544,009, filed Oct. 4, 2006.
U.S. Appl. No. 11/647,530, filed Dec. 27, 2006.
U.S. Appl. No. 11/655,794, filed Jan. 18, 2007.
U.S. Appl. No. 11/725,151, filed Mar. 15, 2007.
U.S. Appl. No. 11/789,704, filed Apr. 24, 2007.
U.S. Appl. No. 11/803,695, filed May 14, 2007.
U.S. Appl. No. 11/925,540, filed Oct. 26, 2007.
U.S. Appl. No. 11/926,326, filed Oct. 29, 2007.
U.S. Appl. No. 11/926,565, filed Oct. 29, 2007.
U.S. Appl. No. 11/928,097, filed Oct. 30, 2007.
U.S. Appl. No. 12/011,100, filed Jan. 23, 2008.
U.S. Appl. No. 12/100,361, filed Apr. 9, 2008.
U.S. Appl. No. 12/117,582, filed May 8, 2008.
U.S. Appl. No. 12/117,672, filed May 8, 2008.
U.S. Appl. No. 12/117,961, filed May 9, 2008.
U.S. Appl. No. 12/118,931, filed May 12, 2008.
U.S. Appl. No. 12/120,902, filed May 15, 2008.
U.S. Appl. No. 12/122,884, filed May 19, 2008.
U.S. Appl. No. 12/340,226, filed Dec. 19, 2008.
U.S. Appl. No. 12/341,602, filed Dec. 22, 2008.
U.S. Appl. No. 12/502,101, filed Jul. 13, 2009.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
USPTO Office Action dated Sep. 16, 2005 in U.S. Appl. No. 10/259,300.
USPTO Office Action dated Jul. 7, 2006 in U.S. Appl. No. 10/259,300.
USPTO Office Action dated Feb. 13, 2007 in U.S. Appl. No. 10/259,300.
USPTO Office Action dated May 29, 2007 in U.S. Appl. No. 10/912,578.
USPTO Office Action dated Oct. 9, 2007 in U.S. Appl. No. 10/259,300.
USPTO Office Action dated Oct. 18, 2007 in U.S. Appl. No. 11/037,548.
USPTO Office Action dated Nov. 14, 2007 in U.S. Appl. No. 10/912,578.
USPTO Office Action dated Nov. 28, 2007 in U.S. Appl. No. 11/234,395.
USPTO Office Action dated Dec. 6, 2007 in U.S. Appl. No. 11/037,548
USPTO Office Action dated Dec. 10, 2007 in U.S. Appl. No. 10/912,578.
USPTO Office Action dated Jan. 24, 2008 in U.S. Appl. No. 10/259,300.
USPTO Office Action dated Apr. 9, 2008 in U.S. Appl. No. 11/037,548.
USPTO Office Action dated Sep. 12, 2008 in U.S. Appl. No. 10/829,917.
USPTO Office Action dated Oct. 6, 2008 in U.S. Appl. No. 10/259,300.
USPTO Office Action dated Oct. 29, 2008 in U.S. Appl. No. 11/347,147.
USPTO Office Action dated Nov. 7, 2008 in U.S. Appl. No. 10/944,270.
USPTO Office Action dated Nov. 17, 2008 in U.S. Appl. No. 10/829,917.
USPTO Office Action dated Nov. 17, 2008 in U.S. Appl. No. 12/117,582.
USPTO Office Action dated Nov. 17, 2008 in U.S. Appl. No. 12/118,931.
USPTO Office Action dated Nov. 25, 2008 in U.S. Appl. No. 12/117,961, filed May 9, 2008.
USPTO Office Action dated Dec. 5, 2008 in U.S. Appl. No. 12/120,902, filed May 15, 2008.
USPTO Office Action dated Jan. 28, 2009 in U.S. Appl. No. 10/944,270.
USPTO Office Action dated Feb. 4, 2009 in U.S. Appl. No. 11/347,147.
USPTO Office Action dated Mar. 3, 2009 in U.S. Appl. No. 12/117,582.
USPTO Office Action dated Mar. 4, 2009 in U.S. Appl. No. 12/118,931.
USPTO Office Action dated Mar. 17, 2009 in U.S. Appl. No. 11/690,127.

USPTO Office Action dated Mar. 18, 2009 in U.S. Appl. No. 10/829,917.
USPTO Office Action dated Mar. 23, 2009 in U.S. Appl. No. 11/804,309.
USPTO Office Action dated Mar. 23, 2009 in U.S. Appl. No. 11/926,326.
USPTO Office Action dated Apr. 21, 2009 in U.S. Appl. No. 10/944,270.
USPTO Office Action dated Jul. 30, 2009 in U.S. Appl. No. 12/118,931.
USPTO Office Action dated Aug. 6, 2009 in U.S. Appl. No. 11/347,147.
USPTO Office Action dated Aug. 6, 2009 in U.S. Appl. No. 12/117,582.
USPTO Office Action dated Aug. 6, 2009 in U.S. Appl. No. 12/117,961.
USPTO Office Action dated Aug. 28, 2009 in U.S. Appl. No. 11/150,847.
USPTO Office Action dated Oct. 21, 2009 in U.S. Appl. No. 12/120,902.
USPTO Office Action dated Nov. 9, 2009 in U.S. Appl. No. 10/829,917.
Bumm, P., H. Kaiser et al 'Cortizontherapie, Corticoide in Klinik and Praxis' Thieme, Stuggart (1992) pp. 390-401 [Summary of textbook].
Cussler, E.L. Diffusion: Mass Transfer in Fluid Systems Cambridge University Press (1996) [Summary of textbook].
Domb, A. et al Handbook of Biodegradable Polymers Harwood Academic Publishers (1997) [Summary of textbook].
ENT Checklist; Physical Examination Performance Checklist [date of publication unknown].
Hosemann W.G. et al Minimally Invasive Endonasal Sinus Surgery Thieme, Stuttgart, New York (2000) [Summary of textbook].
Ingals, E.F. 'New Operation and Instruments for Draining the Frontal Sinus' Ann. Otol Rhinol Laryngol. (1905) vol. 14 pp. 515-519.
Park, K. et al Biodegreadable Hydrogels for Drug Delivery (1993) Technomic Publishing Inc. Lancaster [Summary of textbook].
Schneider. Pfizer Ad for Softip.[date of publication unknown].
Strohm, et al 'Treatment of the Stenoses of the Upper Air Routes by Balloon Dilation' Sudwestdeutscher (Sep. 25, 1999) Abstract 45 pp. 1-3.
Tarasov, D.I. et al. 'Treatment of chronic ethmoiditis by the administration of drugs into the cells of ethmoid labyrinth.' [English Abstract, Journal Article] Vestn Otorinolaringol Nov.-Dec. 1978; (6):45-7.
The Operating Theatre Journal (www.otjonline.com) 'Disposable Medical Device for Wound Disclosure/The Tristel Purple Promotion—A Collaboration between Tristel plc and Karl Storz Endoscopy (UK) Ltd.' pp. 4. [retrieved on Nov. 30, 2011]. Retrieved from the Internet.
Xomed-Treace. Bristol-Myers Squibb. Ad for Laser Shield II. Setting the Standards for Tomorrow [date of publication unknown].
International Preliminary Report on Patentability dated Oct. 4, 2007 from PCT/US06/002004.
International Search Report dated Aug. 29, 2007 re: PCT/US06/02004.
International Search Report dated Mar. 31, 2010 re: PCT/US2009/069143.
International Search Report dated Mar. 31, 2011 re: PCT/US2010/060898.
International Search Report dated Aug. 9, 2011 re: PCT/US2011/038751.
Supplemental European Search Report dated Jul. 1, 2009 re: EP06815285.
Supplemental European Search Report dated Aug. 30, 2011 re: EP06800540.
Supplemental European Search Report dated Sep. 29, 2011 re: EP07750248.
European Search Report dated Sep. 27, 2011 re: EP10182961.

* cited by examiner

ADAPTER FOR ATTACHING ELECTROMAGNETIC IMAGE GUIDANCE COMPONENTS TO A MEDICAL DEVICE

FIELD OF THE INVENTION

The present invention relates generally to medical devices, systems and methods and more particularly to methods and apparatus for attaching electromagnetic image guidance components to guide catheters and other medical devices that are useable in performing therapeutic or diagnostic procedures.

BACKGROUND OF THE INVENTION

Image guided surgery (IGS) procedures (sometimes referred to as "computer assisted surgery") were first developed for use in neurosurgery and have now been adapted for use in certain ENT surgeries, including sinus surgeries. See, Kingdom T. T., Orlandi R. R., *Image-Guided Surgery of the Sinuses: Current Technology and Applications*, Otolaryngol. Clin. North Am. 37(2):381-400 (April 2004). Generally speaking, in a typical IGS procedure, a digital tomographic scan (e.g., a CT or MRI scan) of the operative field (e.g., the nasal cavities and paranasal sinuses) is obtained prior to surgery. A specially programmed computer is then used to convert the digital tomographic scan data into a digital map. During surgery, sensors or markers mounted on the surgical instruments send data to the computer indicating the position of each surgical instrument. The computer correlates the data received from the instrument-mounted sensors with the digital map that was created from the preoperative tomographic scan. One or more image(s) is/are then displayed on a monitor showing the tomographic scan along with an indicator (e.g., cross hairs or an illuminated dot) of the real time position of the surgical instrument. In this manner, the surgeon is able to view the precise position of each sensor-equipped instrument relative to the surrounding anatomical structures shown on the tomographic scan.

The currently available IGS systems fall into two main categories, namely, optical systems and electromagnetic systems. In electromagnetic IGS systems, electromagnetic sensors (e.g., electromagnetic coils) are attached to the surgical instrument and the computer determines the position of the instrument within the body on the basis of signals received from those electromagnetic sensors. Examples of commercially available electromagnetic IGS systems that have been used in ENT and sinus surgery include the ENTrak Plus™ and InstaTrak ENT™ systems available from GE Medical Systems, Salt Lake City, Utah. Other examples of electromagnetic image guidance systems that may be modified for use in accordance with the present invention include but are not limited to those available from Surgical Navigation Technologies, Inc., Louiville, Colo., Biosense-Webster, Inc., Diamond Bar, Calif. and Calypso Medical Technologies, Inc., Seattle, Wash.

The electromagnetic sensors must be attached to the instrument in a manner that maintains the sensors in specific, fixed spatial relationships to the portion of the instrument that is to be tracked within the body. In some cases, the sensor(s) may be built into the instruments at the time of manufacture. In other instances, it may be desirable to attach one or more electromagnetic sensors (or a module containing the sensor(s)) to an instrument immediately prior to or during use of that instrument in a therapeutic procedure.

In the ENT field, one particular area in which it is desirable to attach electromagnetic sensors to instruments is in the performance of procedures where rigid and/or flexible catheters and other devices are inserted through the nose and used to perform sinus surgery or other sinus treatment procedures. One such procedure is balloon dilation of sinus cavity ostia. In such procedure, a guide catheter having a substantially fixed shape is inserted through the nose and advanced to a position where the distal end of the guide catheter is adjacent to the ostium of a paranasal sinus. A guidewire is then advanced through the guide catheter (e.g., Relieva™ Guide Catheter, Acclarent, Inc., Menlo Park, Calif.) and into the paranasal sinus. Thereafter, a balloon catheter (e.g., Relieva™ Balloon Catheter, Acclarent, Inc., Menlo Park, Calif.) is advanced over the guidewire and is used to dilate the ostium of the paranasal sinus, thereby improving drainage from and/or ventilation of that paranasal sinus. Since the guide catheter has a substantially fixed shape, electromagnetic sensors may be mounted on the proximal portion of the guide catheter in positions that bear known spatial relation to the distal end of the guide catheter. In this manner, those proximally mounted sensors may be used in conjunction with an electromagnetic IGS system to track the position of the distal end of the guide catheter within the subject's body. However, to accomplish this, the sensors must be firmly mounted and maintained in specific positions on the proximal end of the guide catheter.

Thus, there remains a need in the art for the development of new adapter devices that may be used to securely attach electromagnetic sensors (or receiver modules that contain the sensor(s)) to guide catheters and/or other devices useable in the performance of balloon dilation procedures as well as other instruments used in ENT and other surgical procedures.

SUMMARY OF THE INVENTION

In accordance with the invention, there is provided an adapter device useable for attaching an electromagnetic image guidance element (the electromagnetic image guidance element can be either a receiver or a transmitter) to a medical device, such as a guide catheter or other device, for example a guide catheter having a balloon, having a distal portion that becomes inserted into the body of a human or animal subject and a proximal portion that remains outside of the subject's body. This adapter device generally comprises (a) a medical device holding fixture constructed to be firmly attached to the proximal portion of the medical device and (b) a element holding fixture constructed to firmly hold the image guidance element in substantially fixed spatial relation to at least one location on the distal portion of the medical device while allowing the distal portion of the medical device to be inserted into the subject's body for purposes of the procedure with a high degree of accuracy.

Further in accordance with the invention, there is provided a method for performing an image guided therapeutic or diagnostic procedure within the body of a human or animal subject. In general this method includes the steps of (a) providing a medical device having a distal portion that is inserted into the subject's body and a proximal portion that remains outside of the subject's body, said medical device being useable to perform or facilitate the performance of at least part of the procedure, (b) providing an IGS system that includes a element which communicates signals to a computing device which uses said signals to determine the location of a device within the body of a human or animal subject, (c) providing an adapter device that includes i) a medical device holding fixture constructed to be firmly attached to the proximal portion of the medical device and ii) a element holding fixture constructed to firmly hold the image guidance element in substantially fixed spatial relation to the distal portion of the medical device while allowing the distal portion of the medical device to be inserted into the subject's body and allowing the medical device to be used to perform or facilitate the performance of at least part of the procedure, (d) attaching the proximal portion of the medical device to the adapter device by way of the medical device holding fixture, (e) attaching the element to the adapter device by way of the element holding fixture, (f) inserting the distal end of the medical device into the subject's body, (g) using the IGS system to guide the positioning of at least one location on the distal portion of the medical device within the subject's body and (h) using the medical device to perform or facilitate the performance of at least part of the procedure. In some embodiments, the IGS system can be used in conjunction with an endoscope and/or a fluoroscope system. In some embodiments of the invention, the medical device may be a guidewire or guide catheter that has a substantially fixed shape and Step H of the method may be carried out by advancing another device over the guidewire or through the guide catheter.

Still further in accordance with the invention there is provided a calibration tool for use in calibrating an IGS system to an elongate medical device that has a substantially fixed shape and a distal end. In general, such calibration tool comprises a substantially rigid body having a receiving groove, a first calibration tip and may include a second calibration tip. In a preferred embodiment, first and second calibration tips extend in 180 degree opposite directions from one another. The elongate medical device (e.g., a curved guide catheter) is insertable into the receiving groove with its distal end positioned in a known position relative to the first and second calibration tips. The first and second calibration tips are alternately placeable in a known location relative to an electromagnetic transmitter such that readings may be taken by the IGS system and used to calibrate the IGS system to the shape of that medical device.

Still further in accordance with the invention there is provided a method for calibrating an image guided surgery system for use with an elongate medical device that has a substantially fixed shape and a distal end. In general, this method comprises the steps of (a) providing a calibration tool comprising a substantially rigid body having a receiving groove, a first calibration tip and a second calibration tip formed therein, said first and second calibration tips extending is 180 degree opposite directions from one another, (b) inserting the medical device into the receiving groove with the distal end of the medical device positioned in a known position within one of said first and second calibration tips, (c) positioning the first calibration tip in a known position relative to an electromagnetic transmitter while obtaining at least one reading using the image guided surgery system, (d) positioning the second calibration tip in a known position in relation to the electromagnetic transmitter while obtaining at least one additional reading using the image guided surgery system and (e) calibrating the image guided surgery system to the substantially fixed shape of the medical device on the basis of the readings obtained in Steps C and D. In some embodiments, multiple readings may be taken in Steps C and D wile maintaining the first and second calibration tips in the known position relative to the electromagnetic transmitter. In some instances, a receiving location (e.g., a well, notch, cavity or other depression) may be formed in the electromagnetic transmitter and the calibrations tips may be maintained in the known location relative to the transmitter by inserting those calibration tips into the receiving location.

Further aspects, details and embodiments of the present invention will be understood by those of skill in the art upon reading the following detailed description of the invention and the accompanying drawings.

DETAILED DESCRIPTION

The following detailed description and the accompanying drawings are intended to describe some, but not necessarily all, examples or embodiments of the invention. The contents of this detailed description and the accompanying drawings do not in any way limit the scope of the invention disclosed herein.

Figure 1:
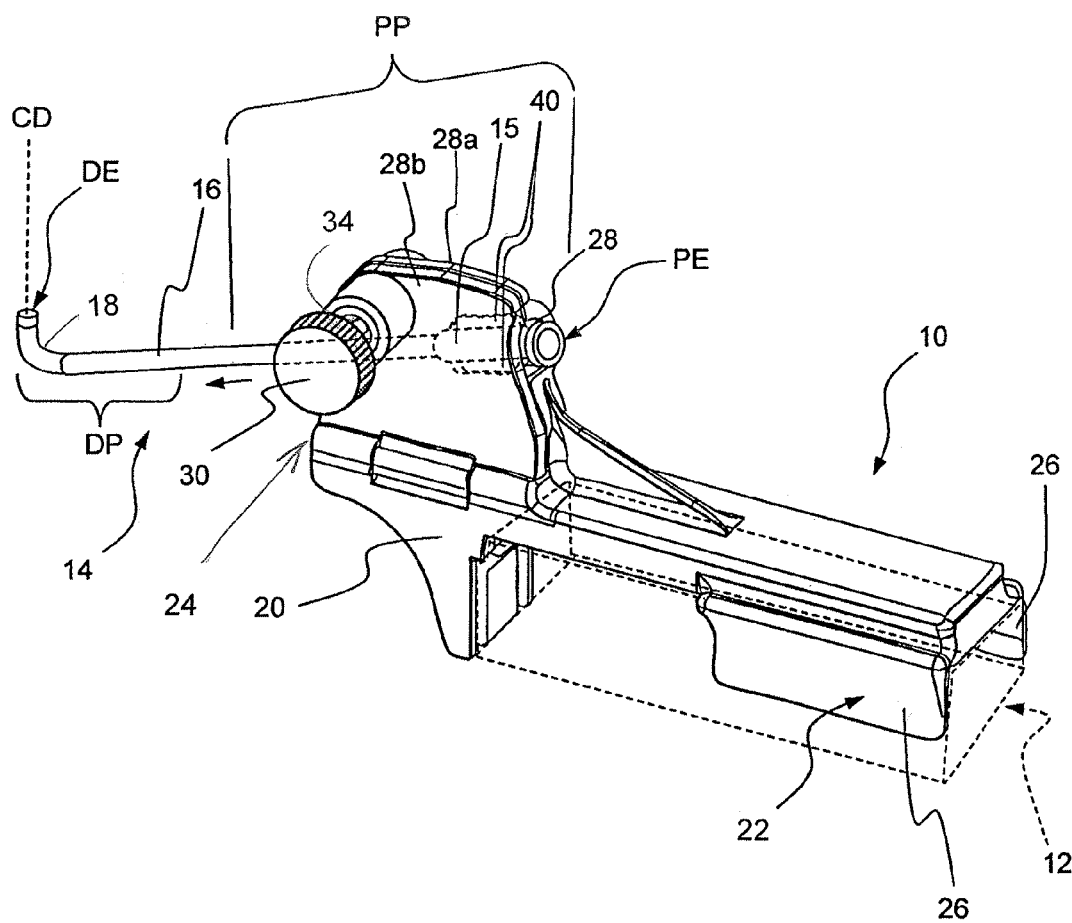
FIG. 1 is a rear perspective view of a system wherein a first embodiment of an adapter device of the present invention is used to attach an electromagnetic image navigation element to a guide catheter.
Figure 2:
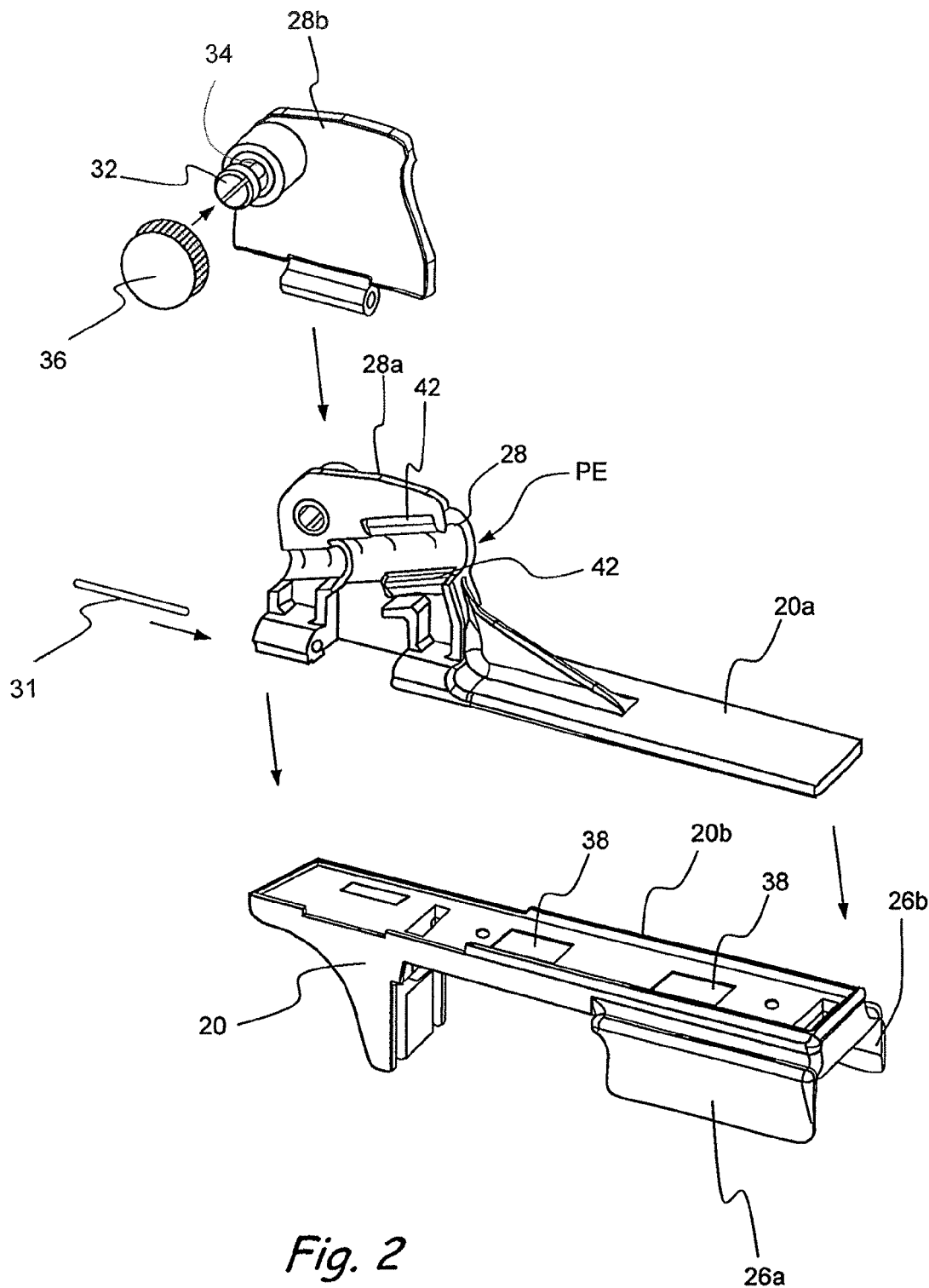
FIG. 2 is an exploded view of components which make up the adapter device shown in FIG. 1.
Figure 3:
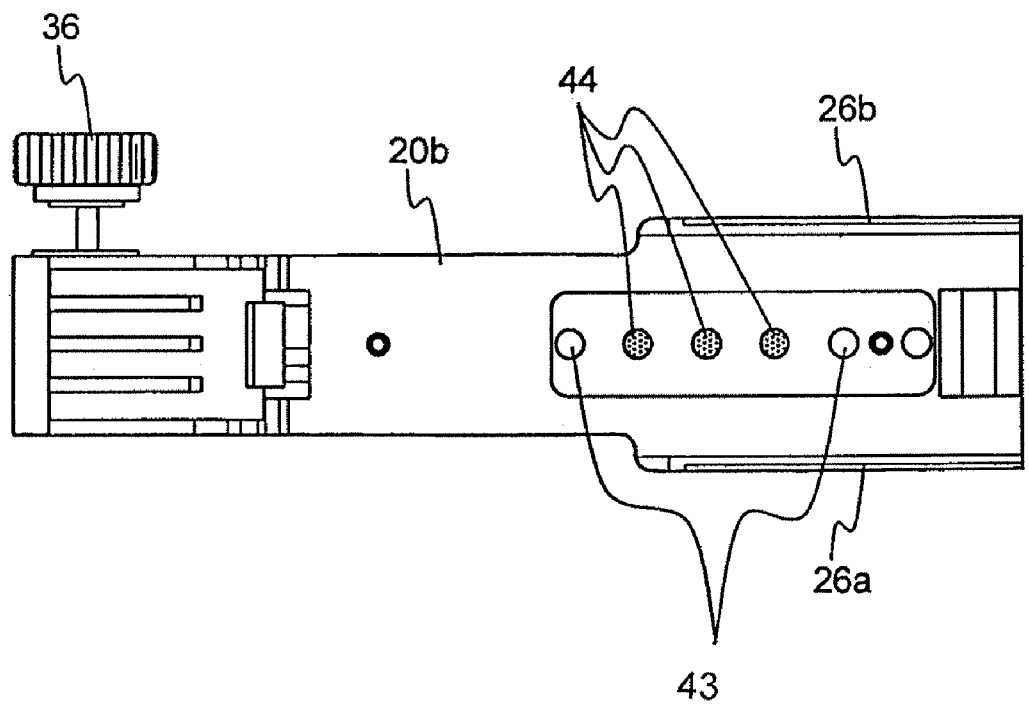
FIG. 3 is a bottom view of the adapter device shown in FIG. 1.

FIGS. 1-3 show an adapter device 10 of the present invention that is designed to facilitate attachment of an electromagnetic image guidance element 12 to a medical device which, in this example, comprises a guide catheter 14. In another embodiment, the medical device can be a stiff member with a dilatation balloon on the distal end. The stiff member can be hollow to allow passage of other medical devices therethrough or to allow suction and/or irrigation therethrough. The guide catheter 14 comprises a tubular shaft 16 having a lumen, an optional curve 18 and an open distal end DE. A Luer hub 15 which may optionally include radially opposing projections 40 is mounted or formed on the proximal end PE of the guide catheter 14. The guide catheter shaft 16 is of substantially fixed size and shape such that the spatial relationship of the distal end DE to the proximal end PE is known. The image guidance element 12 contains electromagnetic sensors that provide signals useable by an IGS system. In typical useage, a distal portion DP of the guide catheter 14 becomes inserted into the subject's body while a proximal portion PP remains outside of the subject's body. The adapter device 10 firmly holds the guide catheter 14 and element 12 such that the electromagnetic sensors located in the element are in substantially fixed spatial relation to the distal end DE of the guide catheter 10. As explained more fully herebelow, this enables the IGS system to track the location of the distal end DE of the guide catheter 10 within the body of a human or animal subject.

One example of a commercially available embodiment of the guide catheter 10 is the Relieva™ Sinus Guide Catheter available from Acclarent, Inc. of Menlo Park, Calif. One example of a commercially available embodiment of an IGS element 12 useable in this invention is the InstaTrak® Receiver available from GE Healthcare, Inc. of Schenectady, N.Y.

With reference to the showings of FIGS. 1-3, one embodiment of the adapter 10 comprises an adapter body 20 having a element holding fixture 22 and a guide catheter holding fixture 24. In this example, the element holding fixture 22 comprises first and second clamping members 26 which are useable to clamp and hold the element 12 in fixed position on the underside of the adapter device body 20, as shown. Also, in this example, the guide catheter holding fixture 24 comprises a guide catheter receiving channel 28 which comprises first guide catheter fixture member 28a and a second guide catheter fixture member 28b. As explained in more detail herebelow, a tightening mechanism 30 which tightens the guide catheter receiving channel 28 about the proximal portion PP of the guide catheter shaft 16, thereby firmly holding the guide catheter 14 in place. In order to facilitate ease of use of the system including creating less interference with an endoscope used by the physician and a comfortable angle for the Physician's hand preferably the guide catheter receiving channel is at an angle between 0 and 45 degrees relative to the element holding fixture, and most preferably at an angle of 20 degrees.

The exploded view of FIG. 2 shows specific components of which this embodiment of the adapter device 10 is assembled. It is to be appreciated that this is merely an example, and various other components/modes of construction may be employed as alternatives to that seen in these figures. As shown, this embodiment of the adapter device 10 comprises an upper body portion 20a that is attached to a lower body portion 20b. Element clamping members 26a, 26b are attached to the lower body portion 20b. A first guide catheter fixture member 28a is formed integrally of the upper body portion 20a and a second guide catheter fixture member 28b is pivotally attached to the upper body portion 20a by way of a hinge which pivots about a pin 30. A screw 32 having a screw head 36 thereon is received within threaded bore 34. Turning of the screw head 36 in a first direction causes the second guide catheter fixture member 28b to pivot toward the second guide catheter fixture member 28a, thereby tightening the guide catheter receiving channel 28 so as to firmly grasp the guide catheter shaft 16. Turning of the screw head 36 in a second direction causes the second guide catheter fixture member 28b to pivot away from the second guide catheter fixture member 28a, thereby widening the guide catheter receiving channel 28 so as to allow the guide catheter shaft 16 to be inserted into or removed from the guide catheter holding fixture 24 or to allow adjustment of the longitudinal position or rotational orientation of the guide catheter 14 relative to the adapter device 10.

The components of the adapter device 20 may be formed of any suitable materials. In some embodiments, the components of the adapter body 20 may be molded from acrylonitrile butadiene styrene (ABS) or other polymeric material having suitable properties. In other embodiments, the components of the adapter body 20 can be metal so as to be resterilizable.

The upper body portion 20a may be attached to the lower body portion 20b in a number of ways including mechanical or frictional connections or, as shown in the example of FIG. 2, by way of adhesive pads 38 using suitable adhesive. In embodiments where the upper and lower body portions 20a, 20b are formed of ABS, a suitable adhesive would be epoxy or cyanoacrylate.

In one embodiment of a method for attaching the guide catheter 14 to the adapter device 10, the screw head 36 is initially turned in a counter-clockwise direction to widen the guide catheter receiving channel 28 to a width wider than the outer diameter of the guide catheter shaft 16. The guide catheter shaft 16 is then inserted through the channel 28 and positioned such that the proximal portion PP if the guide catheter shaft 16 is within the channel 28 and the guide catheter 14 is in the desired rotational orientation. Thereafter, the screw head 36 is turned in the clockwise direction, causing the channel 28 to narrow until sufficient clamping force is exerted on the guide catheter shaft 16 to hold the guide catheter 14 in substantially fixed longitudinal position and to substantially prevent subsequent rotational movement of the guide catheter shaft 16 relative to the adapter device 10. Optionally, in embodiments where opposing radial projections 40 are formed on the Luer hub 15 or elsewhere on the proximal portion PP of the guide catheter 14, corresponding receiving notches 42 may be formed within the guide catheter receiving channel 28, as shown in FIG. 2. The opposing radial projections 40 with be firmly held within notches 42 thereby defining and maintaining the rotational orientation of the guide catheter 14 relative to the adapter device 10. The clamping force of the present invention on the shaft 16 and/or the Luer hub 15 is important to eliminate relative motion between the guide catheter and adapter device 10 and correspondingly the element 12 resulting in very good accuracy in identifying the location of the distal tip of the guide catheter in the patient using the IGS system. In embodiments where the guide catheter shaft 16 includes a curve, the opposing radial projections 40 may extend on a transverse axis TA that is parallel to the direction in which the catheter shaft 16 curves, referred to herein as the "curve direction" CD. In illustration of this concept, in the embodiment of FIG. 1, the catheter shaft 16 has a 90 curve which extends in a particular curve direction CD that is parallel to the transverse axis TA of the opposing radial projections 40. The notches 42 are formed at 12 o'clock and 6 o'clock positions within the guide catheter receiving channel 28. Thus, when the opposing radial projections 40 are held within notches 42 as described, the curve direction CD will be straight up (or straight down) and in this manner the surgeon and the IGS system will at all times be apprised of the rotational orientation of the guide catheter 14.

FIG. 3 shows the underside of the adapter body 20. Indicia indicating specific information on the adapter device 10 (e.g., the size and type of medical device that is to be attached, etc.) may be formed on the underside of the adapter body 20 such that when the element 12 is positioned in the element holding fixture 24, it will recognize or read the indicia provided, and the IGS system may be programmed to make adjustments (e.g., software or computational adjustments) in response to such indicia. In this example, such indicia are in the form of unique magnetic field(s). To create such magnetic field(s), one or more of the magnet receiving slots 43 hold identifying magnet(s) 44 in a manner that creates the desired unique magnetic field(s). The unique identifying magnetic field is sensed by the electromagnetic navigation element 12 and communicated to the IGS system which is programmed to determine, on the basis of such information, the particular type of guide catheter 14 (or other medical device) that is (or will be) attached to the adapter device 10. For example, three identifying magnets 44 fixed to the second, third and fourth magnet slots 43 as shown in FIG. 2 may indicate that the particular curved guide catheter 14 shown in FIG. 1 is attached (or will be attached) to the adapter device 10.

Figure 4:
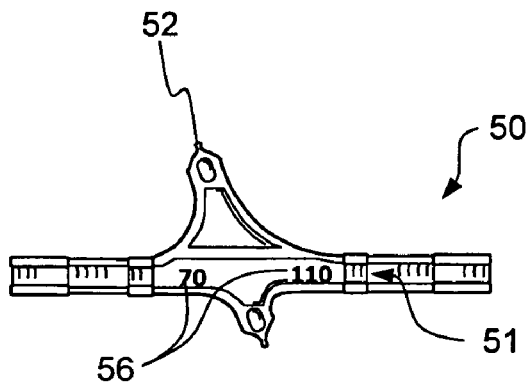
FIG. 4A is a front view of a calibration tool of the present invention.
FIG. 4B is a rear view of the calibration tool of FIG. 4A.
FIG. 4C is a front view of the calibration tool of FIG. 4A in use during a calibration procedure according to the present invention.
Figure 4:
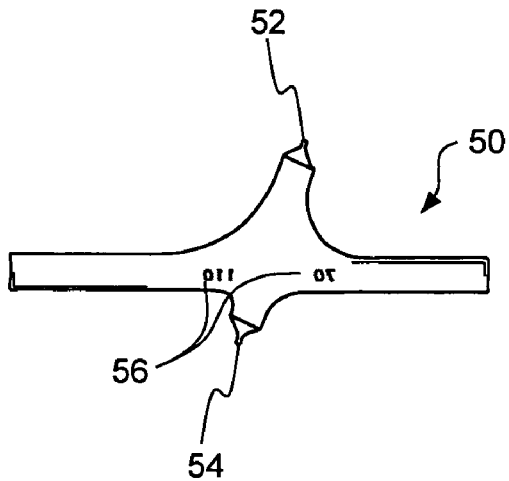
Figure 4:
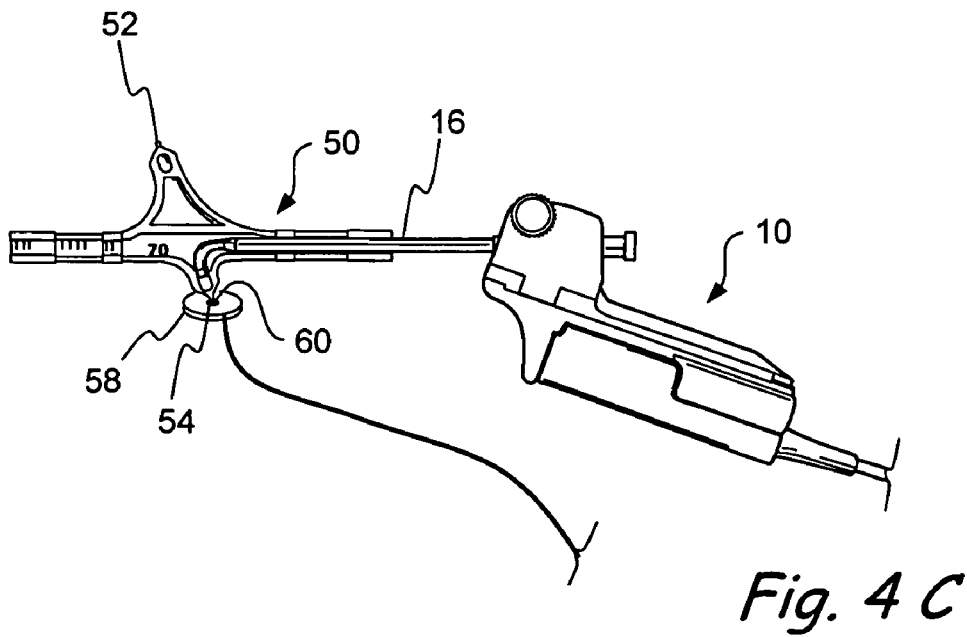

*The position and/or the trajectory of the distal end DE of the guide catheter 14 may be calibrated to an IGS system such as the InstaTrak® surgical image guidance system (available from GE Healthcare, Inc., Schenectady, N.Y.) using a suitable calibration tool. FIGS. 4A-4C show a calibration tool 50 of the present invention which may be used for this purpose. This calibration tool 50 comprises a rigid body having a catheter shaft receiving groove 51 which extends into a first calibration tip 52 on one side and a second calibration tip 54 on the other side. The shaft 16 of guide catheter 14 snap fits into the shaft receiving groove 51 with its distal end DE positioned in second calibration tip 54. An important embodiment of the calibration tool invention of the present application is the use of two calibration tips. The calibration tool in this important embodiment is constructed such that the axis that runs through the two calibration tips is coincident with the axis of the distal opening of the guide device. With this construction when the image guidance system is calibrated to both tips, it is also calibrated to the trajectory extending out from the distal opening of the guide device. Therefore, it is also calibrated to the axis along which a medical device would travel as it exits the distal end of the guide device which prospective trajectory can be displayed on the monitor of the image guidance system. Thus a variety of calibration tools 50 may be designed, each adapted to be used with a particular guide catheter 14 as a result the calibration tool may accommodate a device with only one angle or it may a variety of angled devices. If trajectory is not desired, a calibration tool with only one calibration tip can be used. Alternatively, the system can calibrate trajectory using a single tip calibration tool and a hole of known size and orientation in the headset attached to the patient. Calibration tool 50 may also have one or more guide markings 56 indicating the type of guide catheter 14 that can be used with that calibration tool 50. In a preferred embodiment, guide markings 56 are etched into calibration tool 50.

In the particular embodiment shown in FIGS. 4A-4C, calibration tool 50 is designed to accommodate either of two Relieva™ Sinus Guide Catheters (available from Acclarent, Inc., Menlo Park, Calif.) with curved distal tips curved at 70° and 110° respectively. In typical use with the InstaTrak® IGS system (available from GE Healthcare, Inc., Schenectady, N.Y.) the Relieva™ Sinus Guide Catheter is attached to the adapter device 10 as described above and as shown in FIG. 4C. The catheter shaft 16 is snap fit into the catheter shaft receiving groove 51 such that the distal end DE of the guide catheter shaft 16 is positioned within a tip receiving recess in second calibration tip 54. An imageable headset is attached to the subject's body and an imaging scan is performed to image the headset along with the subject's body using a tomographic imaging modality such as CT, MRI, etc. In a preferred embodiment, the headset is placed on the bridge of the nose and on the external ear canals of the patient. After the imaging scan is completed, the image data is transferred to the InstaTrak® IGS system. Thereafter, at the time of a later medical or surgical procedure, the guide catheter guide 14 and element 12 are attached to the adapter device 10 as described above. Identifying magnets 44 are positioned in the appropriate magnet slots 42 to type of guide catheter 14 being used. The shaft 16 of the guide catheter 14 is snap fit within shaft receiving groove 52 such that the distal end DE of the catheter shaft 16 is positioned within the tip receiving recess of second calibration tip 54. The headset is placed on the patient in the precise location as that used during the tomographic imaging scan. The electromagnetic transmitter 58 is attached to the patient headset. The first calibration tip 52 is then inserted into a tip receiving location, such as a well, cavity, notch or other depression 60 formed on the electromagnetic transmitter 58. Several readings may be taken using the IGS system with varying orientations of guide catheter 14 while keeping first calibration tip 52 within the depression 60 of the transmitter 58. Thereafter, the second calibration tip 54 is fitted into depression 60 of transmitter 58 and several more readings are taken using the IGS system with varying orientations of guide catheter 14 while keeping second calibration tip 54 inside calibration depression 60. In this way, the specific orientation of the curve formed in the catheter shaft 16 is calibrated to the IGS system's computing device. Also, the position of the distal tip of guide device 14 is located at a fixed offset with respect to the position of either calibration tip 52 or 54. The offset is used to calibrate the position of the distal end DE of guide catheter 14 relative to the electromagnetic IGS system. The offset may be programmed into the IGS system or may be manually entered by the IGS system via a user interface such as a keyboard, keypad, touch screen, etc. The IGS system will be programmed to automatically calculate the position and/or the orientation of the distal end DE of the guide catheter 14.

After the calibration process is complete, the guide catheter 14 is removed from the calibration tool 50 and the medical or surgical procedure is conducted.

It is to be understood that the particular design and construction of the adapter device 10 shown in FIGS. 1, 2, 3, 4A, 4B and 4C is not limiting. Various other modes of design and construction may be used within the scope of the invention claimed herein. One of many such examples is shown in FIGS. 5A-5C.

Figure 5A:
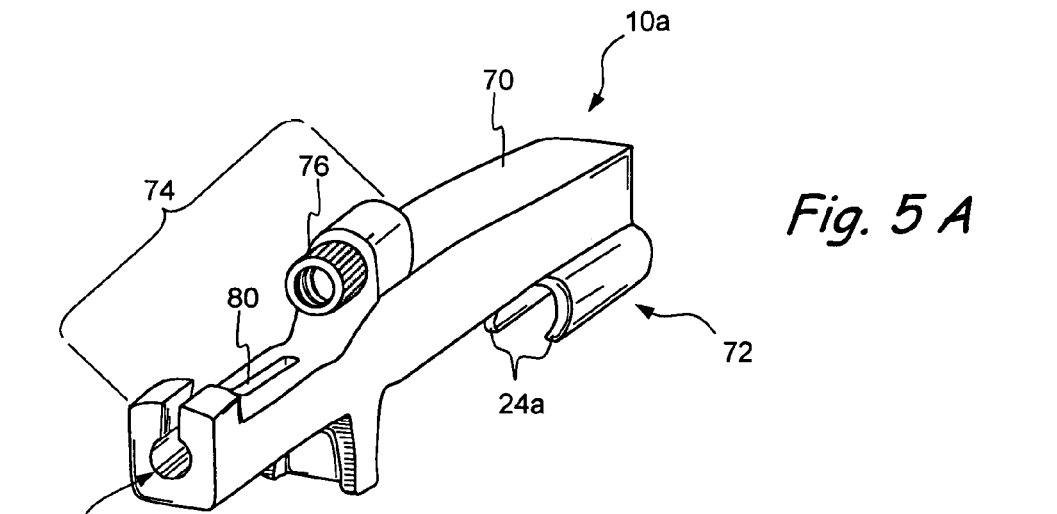
FIG. 5A is a front perspective view of another embodiment of an adapter device of the present invention useable for attaching an electromagnetic image navigation element to a guide catheter.
Figure 5B:
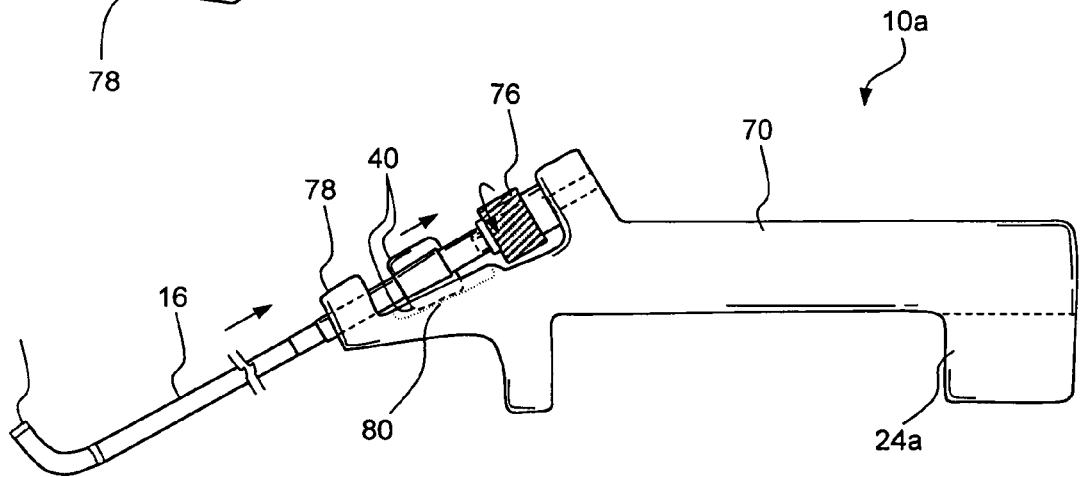
FIG. 5B is a side view of the adapter device of FIG. 5A during the attachment of a guide catheter thereto.
Figure 5C:
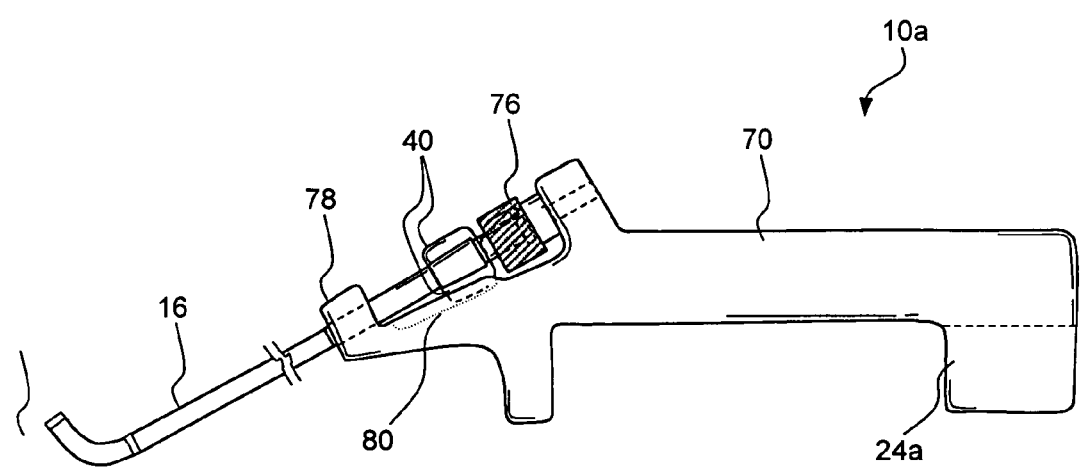
FIG. 5C shows the adapter device of FIG. 5A following attachment of a guide catheter thereto.

With reference to FIGS. 5A-5C, there is shown an alternative adapter device 10a which comprises an adapter body 70 having a element holding fixture 72 and a guide catheter holding fixture 74. In this example, the element holding fixture 72 comprises element clamping members 24a similar to those of the embodiment shown in FIGS. 1-4C for clamping and holding the element 12 in substantially fixed position relative to the adapter device 10a. Also in this example, the guide catheter holding fixture 74 comprises a male Luer connector 76 and a catheter shaft support member 78. As seen in FIGS. 5B and 5C, the proximal portion PP of the guide catheter shaft 16 is inserted into the catheter shaft support fixture 78 and the male Luer connector 76 is connected to the female Luer connector hub 15 on the proximal end of the guide catheter 14. This arrangement firmly holds the guide catheter 14 in substantially fixed position relative to the adapter device 10A. Optionally, a constraining groove 80 may be formed in the adapter body 70 to receive one of the opposing radial projections 40 on the proximal Luer hub 15 of the guide catheter 14, thereby defining and maintaining the rotational orientation of the guide catheter 14 in the same manner as described above with respect to the other embodiment of the adapter device 10. In a further embodiment, the guide catheter 14 can be fixed at any rotational orientation the physician chooses by turning the guide catheter to the desired orientation and then tightening and locking the rotating Luer connector 76 to the proximal Luer hub 15 of the guide catheter 14. In another embodiment, the proximal hub of the guide catheter 14 can have a hexagonal shape or other shape that fits into a matching shaped opening in the adapter device.

The adapter devices of this invention, including the embodiments of the device 10, 10a shown in these drawings, can be used as accessories to the Relieva™ Sinus Guides (Acclarent, Inc., Menlo Park, Calif.) and the InstaTrak™ 3500 Plus and ENTrak™ Plus IGS systems (GE Healthcare, Inc., Schenectady, N.Y.). The combination of the adapter device 10, 10a and the InstaTrak™ 3500 Plus or ENTrak™ Plus IGS system can be used to provide image guidance capabilities to the Relieva™ Sinus Guide for navigation in the paranasal sinus anatomy. This combination can be used to track the distal end DE of the Relieva™ Sinus Guide and/or display its trajectory on a monitor. Specific uses of the adapter device 10, 10*a* include image guided balloon dilation procedures as well as other ear, nose or throat procedures and procedures elsewhere in the body.

It is to be further appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A calibration tool for use in calibrating an image guided surgery system to an elongate medical device that has a substantially fixed shape and a distal end, said calibration tool comprising:
    a substantially rigid body having a receiving groove, a first calibration tip and a second calibration tip;
    the medical device being insertable into the receiving groove with the distal end of the medical device in a known position within one of said first and second calibration tips;
    said first and second calibration tips being alternately placeable in a known location relative to an electromagnetic transmitter.

2. The calibration tool of claim 1 wherein said first and second calibration tips extend in 180 degree opposite directions from one another.

3. A method for calibrating an image guided surgery system for use with an elongate medical device that has a substantially fixed shape and a distal end, said method comprising the steps of:

(A) providing a calibration tool comprising a substantially rigid body having a receiving groove, a first calibration tip and a second calibration tip formed therein;
    (B) inserting the medical device into the receiving groove with the distal end of the medical device positioned in a known position within one of said first and second calibration tips;
    (C) positioning the first calibration tip in a known position relative to an electromagnetic transmitter while obtaining at least one reading using the image guided surgery system;
    (D) positioning the second calibration tip in a known position in relation to the electromagnetic transmitter while obtaining at least one additional reading using the image guided surgery system; and
    (E) calibrating the image guided surgery system to the substantially fixed shape of the medical device on the basis of the readings obtained in Steps C and D.

4. A method according to claim 3 wherein Step C comprises obtaining a plurality of readings with the catheter in differing positions while maintaining the first calibration tip in said known location relative to said electromagnetic transmitter.

5. A method according to claim 3 wherein Step D comprises obtaining a plurality of readings with the catheter in differing positions while maintaining the second calibration tip in said known location relative to said electromagnetic transmitter.

6. A method according to claim 3 wherein a tip receiving location is formed in the electromagnetic transmitter used in Steps C and D and wherein the first and second calibration tips are maintained in known location relative to said electromagnetic transmitter by inserting the first and second calibration tips into said tip receiving location.

7. The method of claim 3 wherein, the first and second calibration tips extend in 180 degree opposite directions from one another.

* * * * *